United States Patent
Gonzales et al.

(10) Patent No.: US 11,160,734 B2
(45) Date of Patent: *Nov. 2, 2021

(54) PERSONAL CARE COMPOSITIONS COMPRISING SHAPED ABRASIVE PARTICLES

(71) Applicant: The Procter & Gamble Company, Cincinnati, OH (US)

(72) Inventors: Denis Alfred Gonzales, Brussels (BE); Martin Ian James, Cincinnati, OH (US); Geert Andre De Leersnyder, Wielsbeke (BE); Steven Ray Merrigan, West Chester, OH (US); Thomas Allen Desmarais, Cincinnati, OH (US); Paul Robert Tanner, Lebanon, OH (US); Binwu Tao, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 809 days.

This patent is subject to a terminal disclaimer.

(21) Appl. No.: 15/494,829

(22) Filed: Apr. 24, 2017

(65) Prior Publication Data

US 2017/0312190 A1    Nov. 2, 2017

Related U.S. Application Data

(63) Continuation of application No. 13/527,686, filed on Jun. 20, 2012, now Pat. No. 9,675,531.

(60) Provisional application No. 61/498,918, filed on Jun. 20, 2011.

(51) Int. Cl.
| | |
|---|---|
| *A61K 8/02* | (2006.01) |
| *A61K 8/81* | (2006.01) |
| *A61Q 19/10* | (2006.01) |
| *A61Q 5/02* | (2006.01) |
| *A61K 8/06* | (2006.01) |

(52) U.S. Cl.
CPC ............ *A61K 8/0279* (2013.01); *A61K 8/062* (2013.01); *A61K 8/8117* (2013.01); *A61Q 5/02* (2013.01); *A61Q 19/10* (2013.01); *A61K 2800/28* (2013.01); *A61K 2800/412* (2013.01)

(58) Field of Classification Search
CPC .... A61K 8/0279; A61K 8/062; A61K 8/8117; A61K 2800/28; A61K 2800/412; A61Q 5/02; A61Q 19/10
See application file for complete search history.

(56) References Cited

U.S. PATENT DOCUMENTS

| | | |
|---|---|---|
| 488,510 A | 12/1892 | Jacob |
| 526,659 A | 9/1894 | Prouty |
| 628,916 A | 7/1899 | Harry |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,694,668 A | 11/1954 | Fricke |
| 3,152,046 A | 10/1964 | Kapral |
| 3,251,800 A | 5/1966 | Cooley et al. |
| 3,332,880 A | 7/1967 | Kessler et al. |
| 3,439,088 A | 4/1969 | Walter |
| 3,818,105 A | 6/1974 | Coopersmith et al. |
| 3,929,678 A | 12/1975 | Laughlin et al. |
| 3,958,581 A | 5/1976 | Abegg et al. |
| 3,962,418 A | 6/1976 | Birkofer |
| 4,032,661 A | 6/1977 | Rowsell et al. |
| 4,089,945 A | 5/1978 | Brinkman et al. |
| 4,136,163 A | 1/1979 | Watson |
| 4,197,865 A | 4/1980 | Jacquet et al. |
| 4,217,914 A | 8/1980 | Jacquet et al. |
| 4,230,688 A | 10/1980 | Rowsell et al. |
| 4,381,919 A | 5/1983 | Jacquet et al. |
| 4,422,853 A | 12/1983 | Jacquet et al. |
| 4,507,280 A | 3/1985 | Pohl et al. |
| 4,529,586 A | 7/1985 | De Marco et al. |
| 4,537,604 A * | 8/1985 | Dawson ............... A61K 8/0275 51/298 |
| 4,663,158 A | 5/1987 | Wolfram et al. |
| 4,677,120 A | 6/1987 | Parish et al. |
| 4,828,542 A | 5/1989 | Hermann |
| 4,885,311 A | 12/1989 | Parish et al. |
| 4,970,252 A | 11/1990 | Sakuta et al. |
| 4,992,476 A | 2/1991 | Geria |

(Continued)

FOREIGN PATENT DOCUMENTS

| | | |
|---|---|---|
| CH | 678488 A5 | 9/1991 |
| CN | 1853606 | 1/2012 |
| EP | 1700619 A1 | 9/2006 |
| FR | 2896678 A1 | 8/2007 |
| JP | 2000-159628 | 6/2000 |
| JP | 2006-282659 | 10/2006 |

(Continued)

OTHER PUBLICATIONS

International Search Report PCT/US2012/043344; dated Dec. 10, 2012; 15 pages.

(Continued)

*Primary Examiner* — Mina Haghighatian
*Assistant Examiner* — Nathan W Schlientz
(74) *Attorney, Agent, or Firm* — John G. Powell; Carrie Schwartz

(57) ABSTRACT

A personal care composition is disclosed comprising abrasive particles. The personal care composition may take a variety of forms such as a leave-on composition or an emulsion and/or may comprise one or more actives or agents.

12 Claims, 2 Drawing Sheets

(56) References Cited

U.S. PATENT DOCUMENTS

| | | | |
|---|---|---|---|
| 5,049,584 A | 9/1991 | Purcell et al. | |
| 5,104,646 A | 4/1992 | Bolich, Jr. et al. | |
| 5,106,609 A | 4/1992 | Bolich, Jr. et al. | |
| 5,124,356 A | 6/1992 | Purcell et al. | |
| RE34,075 E | 9/1992 | Purcell | |
| 5,143,722 A | 9/1992 | Hollenberg et al. | |
| 5,236,986 A | 8/1993 | Sakuta | |
| 5,412,004 A | 5/1995 | Tachibana et al. | |
| 5,413,781 A | 5/1995 | Giwa-Agbomeirele et al. | |
| 5,500,451 A | 3/1996 | Goldman et al. | |
| 5,534,265 A | 7/1996 | Fowler et al. | |
| 5,607,980 A | 3/1997 | McAtee et al. | |
| 5,618,522 A * | 4/1997 | Kaleta | A61K 8/25 424/60 |
| 5,652,228 A | 7/1997 | Bissett | |
| 5,654,362 A | 8/1997 | Schulz, Jr. et al. | |
| 5,658,577 A | 8/1997 | Fowler et al. | |
| 5,674,478 A | 10/1997 | Dodd et al. | |
| 5,681,852 A | 10/1997 | Bissett | |
| 5,686,082 A | 11/1997 | N'Guyen | |
| 5,686,367 A | 11/1997 | Hayashi | |
| 5,720,961 A * | 2/1998 | Fowler | A61Q 5/02 424/401 |
| 5,725,845 A | 3/1998 | Krog et al. | |
| 5,750,122 A | 5/1998 | Evans et al. | |
| 5,753,245 A | 5/1998 | Fowler et al. | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,922,359 A * | 7/1999 | Youssefyeh | A61K 8/19 424/570 |
| 5,939,082 A | 8/1999 | Oblong et al. | |
| 5,993,789 A | 11/1999 | Bonda et al. | |
| 6,113,931 A | 9/2000 | Bonda et al. | |
| 6,126,925 A | 10/2000 | Bonda et al. | |
| 6,159,485 A | 12/2000 | Yu et al. | |
| 6,369,121 B1 | 4/2002 | Catalfamo et al. | |
| 6,524,598 B2 | 2/2003 | Sunkel et al. | |
| 6,696,049 B2 | 2/2004 | Vatter et al. | |
| 6,872,401 B2 | 3/2005 | Seyler et al. | |
| 7,285,570 B2 | 10/2007 | Robinson et al. | |
| 7,357,919 B2 | 4/2008 | Candau | |
| 8,440,602 B2 * | 5/2013 | Gonzales | C11D 17/0013 510/268 |
| 8,440,603 B2 * | 5/2013 | Gonzales | C11D 17/0013 510/130 |
| 8,470,759 B2 * | 6/2013 | Gonzales | C11D 17/0013 510/130 |
| 8,629,095 B2 * | 1/2014 | Deleersnyder | C11D 17/0004 510/395 |
| 8,680,036 B2 * | 3/2014 | Gonzales | A61K 8/025 510/395 |
| 8,703,685 B2 * | 4/2014 | Gonzales | C11D 17/0013 510/130 |
| 8,759,270 B2 * | 6/2014 | Perez-Prat Vinuesa | C11D 3/2072 134/25.2 |
| 8,852,643 B2 * | 10/2014 | Gonzales | A61Q 5/02 424/401 |
| 9,616,002 B2 * | 4/2017 | Gonzales | A61K 8/8152 |
| 9,717,674 B1 * | 8/2017 | Guskey | A61K 8/8164 |
| 2002/0041889 A1 | 4/2002 | Masuda et al. | |
| 2002/0131948 A1 | 9/2002 | Toumi et al. | |
| 2002/0182237 A1 | 12/2002 | Bissett et al. | |
| 2003/0108492 A1 | 6/2003 | Chaudhuri | |
| 2003/0157035 A1 | 8/2003 | Chaudhuri | |
| 2004/0057912 A1 | 3/2004 | Bonda | |
| 2004/0057914 A1 | 3/2004 | Bonda | |
| 2004/0057916 A1 | 3/2004 | Bonda | |
| 2004/0057920 A1 | 3/2004 | Focht et al. | |
| 2004/0062726 A1 | 4/2004 | Bonda et al. | |
| 2004/0136943 A1 * | 7/2004 | Tomokuni | A61K 8/39 424/70.31 |
| 2004/0170586 A1 | 9/2004 | Ferrari et al. | |
| 2004/0219119 A1 | 11/2004 | Wei et al. | |
| 2005/0020727 A1 | 1/2005 | Shriver et al. | |
| 2005/0130873 A1 | 6/2005 | Cheung et al. | |
| 2006/0034875 A1 | 2/2006 | Nakanishi et al. | |
| 2006/0134045 A1 | 6/2006 | Cao et al. | |
| 2006/0147396 A1 | 7/2006 | Monello | |
| 2006/0177816 A1 | 8/2006 | Caruso et al. | |
| 2007/0020220 A1 | 1/2007 | Osborne | |
| 2007/0039103 A1 | 2/2007 | Godfrey | |
| 2007/0297996 A1 | 12/2007 | Tanner | |
| 2008/0019930 A1 | 1/2008 | Candau et al. | |
| 2008/0139433 A1 | 6/2008 | Mock et al. | |
| 2008/0145324 A1 | 6/2008 | Richard et al. | |
| 2009/0247444 A1 | 10/2009 | Ruppert et al. | |
| 2009/0311159 A1 | 12/2009 | Gray | |
| 2010/0081604 A1 | 4/2010 | Barger et al. | |
| 2010/0081605 A1 | 4/2010 | Barger et al. | |
| 2010/0081606 A1 | 4/2010 | Barger et al. | |
| 2010/0112100 A1 | 5/2010 | Willemin et al. | |
| 2010/0183529 A1 | 7/2010 | Richard et al. | |
| 2010/0189669 A1 | 7/2010 | Hakozaki | |
| 2011/0059143 A1 | 3/2011 | Iavarone et al. | |
| 2011/0150787 A1 * | 6/2011 | Gonzales | A61Q 11/00 424/49 |
| 2011/0150788 A1 * | 6/2011 | Gonzales | A61Q 11/00 424/49 |
| 2011/0150949 A1 * | 6/2011 | Gonzales | C11D 17/0013 424/401 |
| 2011/0150950 A1 * | 6/2011 | Gonzales | A61Q 5/02 424/401 |
| 2011/0150951 A1 * | 6/2011 | Gonzales | A61K 8/025 424/401 |
| 2011/0262371 A1 | 10/2011 | Deleersnyder et al. | |
| 2011/0262504 A1 | 10/2011 | Dekeersnyder et al. | |
| 2013/0039961 A1 | 2/2013 | Gonzales et al. | |

FOREIGN PATENT DOCUMENTS

| | | |
|---|---|---|
| JP | 2007262029 A | 10/2007 |
| JP | 47882891 | 9/2011 |
| WO | 9114420 A1 | 10/1991 |
| WO | 9323028 A1 | 11/1993 |
| WO | 02076423 A5 | 12/2002 |
| WO | 2004024798 A1 | 3/2004 |
| WO | 2009023765 A1 | 2/2009 |
| WO | 2010039571 A1 | 4/2010 |
| WO | 2010039572 A1 | 4/2010 |
| WO | 2010039574 A1 | 4/2010 |
| WO | 2011133438 A1 | 10/2011 |
| WO | 2011133508 A1 | 10/2011 |
| WO | 2012084423 A2 | 6/2012 |

OTHER PUBLICATIONS

All Office Actions, U.S. Appl. No. 13/527,686.
Database GNPD [Online] MINTEL, Dec. 2008,, 3 Pages, Database Accession No. 1021001.

* cited by examiner

PERSONAL CARE COMPOSITIONS COMPRISING SHAPED ABRASIVE PARTICLES

FIELD OF THE INVENTION

Personal care compositions are disclosed comprising shaped abrasive particles having unique shape and form.

BACKGROUND OF THE INVENTION

Personal care compositions routinely include particulate material for a variety of purposes. One function for such particles is to provide a cleansing benefit. Many particles are commonly used for this purpose and include inorganic materials like carbonate salt, clay, silica, silicate, shale ash, perlite and quartz sand or organic materials like polypropylene, polyethylene, polymethylsilsesquioxane, nylon, polyacrylate and the like, which are often supplied as a powder or bead.

The problem with conventional materials is that while some scouring of a substrate may be desired for cleansing efficacy, keratinous tissues such as the skin are susceptible to damage from overly abrasive particles. Furthermore, such particles often have an undesirable texture for personal care compositions. For example, consumers selecting a facial cleanser may avoid compositions that feel gritty or coarse. Conversely, less aggressive particles may yield poor cleansing performance as evidenced by soil or make-up remaining on the skin after use of the composition. Formulators often must choose between over abrasive particles that may cause surface damage and have a poor feel profile but scour well and gentler particles with a better feel profile but with reduced cleansing efficacy.

A similar problem exists with personal care compositions having an exfoliation or microdermabrasion benefit. Selection of suitable particles often requires a chose of undesirable feel or limited efficacy.

In response to these problems, a need exists for new abrasive particles that may resolve the problem identified above as well as other issues related to the formulation of personal care compositions.

SUMMARY OF THE INVENTION

A personal care composition for cleansing keratinous tissue may comprise abrasive particles having two or more parameters selected from a mean Equivalent Circle diameter of between 10 µm to 1000 µm, 50 µm to 500 µm, 75 µm to 350 µm, or 100 µm to 250 µm; a mean Circularity of between 0.10 to 0.50 or between 0.35 to 0.45; a mean Solidity of between 0.40 to 0.90, 0.70 to 0.90, or 0.45 to 0.85; a mean Roughness between 0.05 to 0.30 or between 0.05 to 0.15; a packing density of between 10 to 250 kg/m$^3$, 50 to 150 kg/m$^3$, 60 to 120 kg/m$^3$, or 70 to 100 kg/m$^3$; or a hardness of between 5 to 50 kg/mm$^2$ or 15 to 25 kg/mm$^2$. The personal care composition further comprises from about 1% to 10%, by weight of the composition, of a detersive surfactant; and a dermatologically acceptable carrier.

A personal care composition in the form of an emulsion having an oil phase and an aqueous phase may also comprise the aforementioned abrasive particles.

A personal care composition may comprise the aforementioned abrasive particles in addition to a dermatologically acceptable carrier and an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, and combinations thereof.

BRIEF DESCRIPTION OF THE FIGURES

FIG. 3A is an illustration of a particle.
FIG. 3B is a magnified illustration of the edge of the particle shown in FIG. 3a.

DETAILED DESCRIPTION OF THE INVENTION

Figure 1:
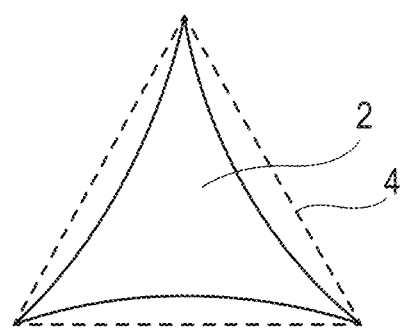
FIG. 1 is an illustration a particle showing a convex hull.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the components described herein. As used herein, "consisting essentially of" means that the composition or component may include additional ingredients, but only if the additional ingredients do not materially alter the basic and novel characteristics of the claimed compositions or methods.

The term "personal care composition" means compositions suitable for topical application on mammalian keratinous tissue.

The term "apply" or "application," as used in reference to a composition, means to apply or spread the compositions of the present invention onto keratinous tissue such as the epidermis.

The term "keratinous tissue" refers to keratin-containing layers disposed as the outermost protective covering of mammals (e.g., humans, dogs, cats, etc.) which includes, but is not limited to, skin, lips, hair, toenails, fingernails, cuticles, hooves, etc.

The term "dermatologically acceptable" means that the compositions or components described are suitable for use in contact with human skin tissue without undue toxicity, incompatibility, instability, allergic response, and the like.

The term "safe and effective amount" means an amount of a compound or composition sufficient to significantly induce a positive benefit.

The term "leave-on," in reference to compositions, means a composition intended to be applied to and allowed to remain on the keratinous tissue. These leave-on compositions are to be distinguished from compositions which are applied to the skin and subsequently (in a few minutes or less) removed either by washing, rinsing, wiping, or the like. Leave-on compositions exclude rinse-off applications such as shampoos, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying or other processing surfactants that are not intended to provide any significant cleansing benefits when applied topically to the skin.

The term "derivatives" means an ester, ether, amide, hydroxy, and/or salt structural analogue of the relevant compound.

The term "to structure" or "structure" means to increase viscosity, yield, thicken, solidify, or provide solid or crystalline structure to the personal care composition The term "soluble" means at least about 0.1 g of solute dissolves in 100 ml of solvent, at 25° C. and 1 atm of pressure.

Abrasive Particles

The abrasive particles maybe made of a variety of materials or mixture of materials. Suitable materials include organic or inorganic salt abrasives such as carbonate-derived salts, phosphate-derived salts, pyrophosphate-derived salts, silica or alumina derived salts, hydroxyapatite, diatomaceous, fuller earth, talc, etc., polymeric abrasives containing polyethylene, polypropylene, PVC, polycarbonate, melamine, urea, polyurethane, polyacrylate, polystyrene, phenolic, polyesters, polyamide, or natural abrasives derived from cellulose, lingo-cellulose or shell such as nut shell, apple seeds, olive stones, apricot seed, kernel, wood, bamboo and plants.

In select embodiments, the abrasive particles are made from the polymeric material selected from the group consisting of polyethylene, polypropylene, PVC, polycarbonate, melamine, urea, polyurethane, polyacrylate, polystyrene, phenolic, polyesters, polyamide and mixtures thereof so as to include both homopolymers and copolymers. In other embodiments, the abrasive particles are made from natural abrasives derived from cellulose, lingo-cellulose or shell such as nut shell, apple seeds, olive stones, apricot seed, kernel, wood, bamboo and plants and mixtures thereof.

Shearing or graining methods may be used to reduce the above materials to abrasive particles featuring the distinct particle parameters as described in detail below. Grain shaping methods include agglomerating, printing, carving, etc. Other shaping processes include mixing the abrasive materials in as fillers within a thermoplastic or solidifying matrix. Other reduction techniques include milling, grinding, cutting, and the like.

One technique to create the abrasive particles is by way of foaming the abrasive material itself or by foaming the abrasive material dispersed within a matrix. The resultant foam is reduced into abrasive particles with having the distinct particle parameters described below. Foaming processes and foam structure are typically achieved via gas expansion process (e.g., either by injecting gas or solvent within the abrasive precursor and allowing expansion by pressure drop) and/or increasing of temperature (e.g., extrusion foaming process or with in-situ generated gas followed by hardening of the abrasive precursor such as a polyurethane foaming process). Alternatively, foam structures can also be achieved via emulsion process, followed by hardening and drying step. The foams may have either a closecell or open-cell structures. It is believed that improved cleaning effect can be achieved with abrasive particle created from an open-cell foam.

In certain embodiments, suitable abrasive particles may be made from a foam having density of greater than 100 $kg/m^3$ or, alternately, 500 $kg/m^3$. In other embodiments, a better cleaning effect can be achieved with the foam density being below 500, 250, 100, 75, or 50 $kg/m^3$ and above 5, 10, 25, or 50 $kg/m^3$.

It may be desirable that the foam has sufficient brittleness to favor the reduction of the foam into particles (i.e., upon stress, the foam has little tendency to deform but rather break into particles). A suitable foam may have no-detectable phase transition (e.g., glass transition or melting temperature) or may have a phase transition temperature significantly higher that the usage temperature. A suitable phase transition temperature may be at least 20 OC or 40 OC above the usage temperature for a composition containing the abrasive particle.

The foam may be reduced into the abrasive particles herein by grinding or milling the foam. Other suitable means include the use of eroding tools such as a high speed eroding wheel with dust collector wherein the surface of the wheel is engraved with a pattern or is coated with abrasive sandpaper or the like to promote the foam to form the abrasive particles herein. In certain embodiments, the abrasive particles obtained via reduction methods are single particles that do not have residual cell structure.

Particles may be produced by grinding the foam structure to target size and shape as described herein. The foam cell size may be a factor to yield particles of a particular. For example, if a large particle size is desired, a foam with a large cell size may be used and vice versa. Additionally, in order to preserve an optimal particle shape while reducing the foam structure into a particle, it is advisable that the target particle size is not excessively below the dimension of the cell size of the foam. For example, the target particle size is one embodiment is not below about half of the foam cell size.

The foam may be reduced to particles in several stages. For example, the foam may first be broken into pieces of a few cm in dimension by manually chopping or cutting, or using a mechanical tool such as a lumpbreaker, for example the Model 2036 from S Howes, Inc. of Silver Creek, N.Y. In a second stage, the lumps may be agitated using a propeller or saw toothed disc dispersing tool. In a third stage, a high shear mixer (such as the Ultra Turrax rotor stator mixer from IKA Works, Inc., Wilmington, N.C.) can be employed to reduce the particle size. The second and third stages may be performed with the foam dispersed in a carrier.

A suitable foam for use in creation of the abrasive particles is styrene foam. The styrene foam may be formed with a polymer comprising styrene monomeric units and, optionally, other comonomers. In a particular embodiment, the abrasive particles comprise a covalently cross-linked copolymer of styrene-co-divinyl benzene. By "covalently cross-linked copolymer of styrene-co-divinyl benzene" it is meant herein a copolymer comprising mono-functional and multi-functional monomeric units such as di-functional monomeric units, all derived from the vinyl benzene structure, copolymerized to form a covalently cross-linked network structure. Other suitable divinyl benzene cross-linked styrene polymers include copolymers of styrene and divinyl benzene as well as at least one additional monomeric unit, such as alkyl vinyl benzenes, for example ethyl styrene, or alkyl esters of acrylic or methacrylic acid and mixtures thereof.

The principal monomeric components of the copolymer are styrene, various structural isomers (ortho, meta, para substituted) of divinyl benzene and various structural isomers (ortho, meta, para substituted) of ethyl, as well as vinyl benzene. The latter is a by-product of the manufacture of divinyl benzene, present in varying amounts depending on the supply source. Divinyl benzene provides covalent cross-links in the network structure via incorporation of each of its polymerizable vinyl groups into different propagating polymer chains. For a formulation comprising equal parts of Styrene to DVB 55 (a mixture of divinyl benzene and ethyl vinyl benzene in the weight ratio of 55:45, commercially available from the Dow Chemical Co.) there is approximately one difunctional monomer for every three monofunctional monomers. Alternatively, monomers based on chemical structures bearing styrene or divinyl benzene type of chemical structures can also be prepared alone or copolymerized with styrene or divinyl benzene into abrasive particles.

Suitable covalently cross-linked copolymers of styrene-co-divinyl benzene comprise about 20% or 40% to about 60% or 80% of styrene and the balance of divinyl benzene and ethyl styrene in the weight ratio of 55:45 (Commercially available as DVB 55 from the Dow Chemical Co.).

The covalently cross-linked copolymer of styrene-co-divinyl benzene polymer may be obtained by any suitable means known to those skilled in the art. A suitable production route for production of the foam is to form a water/oil High Internal Phase Emulsion (HIPE) of water in the monomer mixture and polymerize in-situ, as described in U.S. Pat. No. 6,369,121 (in particular, the section directed to the making of a water/oil High Internal Phase Emulsion as well as the apparatus for use therein). In this embodiment, said water/oil High Internal Phase Emulsion may be obtained by a method for continuous, once-through production of a high internal phase emulsion, the method comprising the steps of: a) providing a first phase; b) providing a second phase, wherein said second phase is substantially immiscible with said first phase and the ratio of said first phase to said second phase is between about 2:1 and about 250:1; c) processing said first and second phases using a first static mixer, having at least one segment, in a single pass so as to provide sufficient shear to emulsify said first phase in said second phase creating said high internal phase emulsion (HIPE) having a internal phase size distribution with a mean particle size. The method may further comprise a step wherein a portion of said processed HIPE is re-circulated from said outlet of said static mixer and introduced into said inlet where said processed HIPE is processed with the first phase and the second phase.

The first phase may be a water phase including a free radical initiator. The free radical initiator herein can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts. The free radical initiator is preferably present at up to about 20 mole percent based on the total moles of polymerizable monomers in the oil phase. The initiator may be present in an amount of from about 0.001 to 10 mole percent based on the total moles of polymerizable monomers in the oil phase.

The second phase may be the oil phase. The oil phase may comprise from about 80% to about 98% by weight, of the polymerizable monomers, and may comprise from about 2% to about 20% by weight of, an emulsifier which is soluble in the oil phase and which is suitable for forming a stable water-in-oil emulsion. Suitable emulsifiers for use herein can include any of a number of conventional emulsifiers applicable for use in low and mid-internal-phase emulsions. Suitable emulsifiers include nonionic materials and can have a wide range of HLB values. Examples of some typical emulsifiers include sorbitan esters such as sorbitan laureates (e.g., SPAN® 20), sorbitan palmitates (e.g., SPAN® 40), sorbitan stearates (e.g., SPAN® 60 and SPAN® 65), sorbitan monooleates (e.g., SPAN® 80), sorbitan trioleates (e.g., SPAN® 85), sorbitan sesquioleates (e.g., EMSORB® 2502), and sorbitan isostearates (e.g., CRILL® 6); polyglycerol esters and ethers (e.g., TRIODAN® 20); polyoxyethylene fatty acids, esters and ethers such as polyoxyethylene (2) oleyl ethers, polyethoxylated oleyl alcohols (e.g. BRIJ® 92 and SIMUSOL®92), etc.; mono-, di-, and triphosphoric esters such as mono-, di-, and triphosphoric esters of oleic acid (e.g., HOSTAPHAT KO3OON), polyoxyethylene sorbitol esters such as polyoxyethylene sorbitol hexastearates (e.g., TLAS® G-1050), ethylene glycol fatty acid esters, glycerol mono-isostearates (e.g., IMWITOR 780K), ethers of glycerol and fatty alcohols (e.g., CREMOPHOR WO/A), esters of polyalcohols, synthetic primary alcohol ethylene oxide condensates (e.g., SYNPERONIC A2), mono and diglycerides of fatty acids (e.g., ATMOS® 300), and the like. Other preferred emulsifiers include the diglycerol esters derived from monooleate, monomyristate, monopalmitate, and monoisostearate acids.

For preferred HIPEs herein, the emulsifiers include sorbitan monoesters of branched C16-C24 fatty acids, linear unsaturated C16-C22 fatty acids, and linear saturated C16-C24 fatty acids, such as sorbitan monooleate, sorbitan monomyristate, and sorbitan monoesters derived from coconut fatty acids; diglycerol monoesters of branched C16-C24 fatty acids, linear unsaturated C16-C22, fatty acids, or linear saturated C12-C14 fatty acids, such as diglycerol monooleate (i.e., diglycerol monoesters of C18:1 fatty acids), diglycerol monomyristate, diglycerol monoisostearate, and diglycerol monoesters of coconut fatty acids; diglycerol monoaliphatic ethers of branched C16-C24 alcohols (e.g. Guerbet alcohols), linear unsaturated C16-C22 alcohols, and linear saturated C12-C14 alcohols (e.g., coconut fatty alcohols), and mixtures of these emulsifiers. Other emulsifiers include polyglycerol ester emulsifiers described in U.S. Pat. No. 5,287,207 and polyglycerol ether emulsifiers described in U.S. Pat. No. 5,500,451. Another suitable emulsifier is described in U.S. Pat. No. 6,444,716. Such emulsifiers comprise a composition made by reacting a hydrocarbyl substituted succinic acid or anhydride or a reactive equivalent thereof with either a polyol (or blend of polyols), a polyamine (or blend of polyamines) an alkanolamine (or blend of alkanol amines), or a blend of two or more polyols, polyamines and alkanolamines. The lack of substantial carbon-carbon unsaturation rendering them substantially oxidatively stable.

The produced HIPE emulsion may be heated (e.g., to at least about 65° C., about 80° C., or about about 95° C.) to initiate the free radical polymerization and may be cured until substantially all of the monomer (at least about 99%) has been converted to polymer. A gradual gradient of temperature, rising from the mix temperature to an elevated temperature, for example rising to about 95° C. over a period of 30 minutes is also feasible. The result foam is reduced according to techniques described above.

In another embodiment, the abrasive particles may be produced from polyurethane foam. The polyurethane foam may be the reaction product of diisocyanate monomers and polyols, in the presence of catalyst. The diisocyanate monomer can be aliphatic and/or aromatic. Polyurethane foams can be made with varying density and hardness by varying the type of diisocyanate monomer(s) and polyols and by adding other substances to modify these characteristics. Other additives can be used to improve the stability of the polyurethane foam and other properties of the polyurethane foam.

The choice of diisocyanate affects the stability of the polyurethane upon exposure to light. Polyurethane foams made from aromatic diisocyanates yellow with exposure to light, whereas those made from aliphatic diisocyanates are color-stable. Due the discoloration of the polyurethane foam containing aromatic diisocyanates, aliphatic diisocyanates may be used in production of polyurethane foam. However by mixing aliphatic and aromatic diisocyanate monomers and keeping the aromatic diisocyanate monomer levels below 60%, 50%, or 40% of the weight of the diisocyanates, color-stable polyurethane foam can be provided for the use as abrasives particles.

Suitable aromatic diisocyanate monomers include toluene diisocyanate (TDI), methylene dianiline diisocyanate (MDI), polymeric forms of MDA, polymeric form of TDI, and mixtures thereof. Suitable aliphatic diisocyanate monomers include hexamethylene diisocyanate (HDI), dicyclohexyl methane diisocyanate (H12MDI), isophorone diisocyanate (IPI), lysine or lysine ester diisocynate (LDI), trimers of previous and mixtures thereof.

Example of suitable polyols include castor and/or soybean oil (including ethoxylated or propoxylated oils, including sulfated oils); sugars and polysugars such as glucose, sucrose, dextrose, lactose, fructose, starch, cellulose; sugar alcohols such as glycol, glycerol, erythritol, thereitol, arabitol, xylitol, ribitol, mannitol, sorbitol, dulcitol, iditol, isomalt, maltitol, lactitol, polyglycitol and trimethylolpropane. Other useful polyols formed by the reaction of previous polyols (including derivative from toluene dianiline) with diethanol amine and propylene oxide (a non-exhaustive example is "sucrose" propoxylate).

Other suitable polyols to be used are aliphatic or aromatic glycols such as ethylene glycol and polymeric derivatives such as polyethylene glycol diol, propylene glycol and polymeric derivatives such as polypropylene glycol diol, tetratmethylene glycol and polymeric derivatives such as polytetramethylene glycol.

Polyester polyols are also suitable polyols and polyester polyols resulting from the reaction of acids (adipic, succinic, dodecandioc, azelaic, phtalic anhydride, isophthalic, terephtalic) and alcohols (ethylene glycol, 1,2 propylene glycol, 1,4 butane diol, 2-CH3-1,3-propane diol, neopentyl glycol, diethylene glycol, 1,6-hexanediol, trimethylol propane, glycerin). Non-exhaustive examples are polyethylenediol adipate, polypropylenediol adipate, polybutanediol adipate.

Other suitable polyols are polyethylene terephtalate and co-polymers derivatives such as polytheylene terephtalate glycols, acrylic polyols, polycarbonate polyols, polyols derived from dimethyl carbonate reacted with polyols such as hexanediol, mannich polyols and amine terminated polyols and polycaprolactone polyols and mixtures thereof.

Mixtures of previous alcohols are at times desirable to achieve the right chemical and mechanical properties of the polyurethane foams.

In certain embodiments, the polyols ethylene glycol, glycerol, polyethylene glycol, polypropylene glycol, polytetramethylene glycol, polycaprolactonediol, poly(ethylene adipate)diol, poly(hexamethylene adipate)diol, castor oil, soy bean oil, sugars and polysugars and mixtures thereof.

The choice of polyol may have an effect on the biodegradability and the hardness of the polyurethane foam. For instance, in order to achieve the manufacture of biodegradable foams, hydrophilic polyols may be desirable such as ethyleneglycol-based or caprolactone-based-polyols and/or polyols containing cleavable ester or carboxylic anhydride function such as adipate-based polyols, optionally mixed with natural polyols such as sugars and sugar alcohol derivatives, castor oil and mixtures thereof. In a particular embodiment, a biodegradable polyurethane foam may use polyols having molecular weight from 400 to 4000 selected from the group consisting of polycaprolactonediol, polyethyleneglycol, poly(ethyleneadipate) diol, poly (hexamethylene adipate) diol and mixtures thereof. Furthermore, the addition of bioactive or biodegradable material during the foaming process may also yield polyurethane with sufficient biodegradability.

Exemplary additives include lignin, molasses, polyhydroxyalkanoates, polylactide, polycaprolactone, or aminoacid.

The use of low molecular weight polyols with rigid molecular structure may increase the overall hardness of the polyurethane foam. In certain embodiments, useful polyols to produce hard polyurethane foams may have an average molecular weight ($M_w$) below 2000, 1500 or 1000. Suitable polyols include sucrose, ethylene glycol, glycerol, polyethylene glycol ($M_w$<400) and mixtures thereof. Additionally, in order to increase the hardness of the polyurethane foam, the use of polyols with high alcohol (or amine) function content may be desired. Polyols functionality defined by the OH number in mg KOH/g polyol may be above 150, 200, or 300. Hydrolytic stability is a preferred feature of the polyurethane foam when compositions are formulated in pH below 4 and in pH above 9. Suitable polyols providing hydrolytic stability are polycarbonates.

The polyurethane foam may be created with mostly closed foam cells or mostly open foam cells. In one embodiment, the foam has an open cell structure. The resultant foam is reduced according to techniques described above.

In another embodiment, the abrasive particles may be produced from melamine foam. A suitable melamine foam is a melamine-formaldehyde resin foam. A suitable melamine-formaldehyde resin foam is commercially available under the trade name Basotect® from BASF.

Melamine foam may be prepared by blending the reactant materials of melamine and formaldehyde, or a precursor thereof, with a blowing agent, a catalyst and an emulsifier, injecting the resultant mixture into a mold, and making the reaction mixture generate heat through a proper means such as heating or irradiation with electromagnetic wave to cause foaming and curing. The molar ratio of melamine to formaldehyde (i.e., melamine:formaldehyde) for producing the precursor is may be about 1:1.5 to about 1:4 or about 1:2 to about 1:3.5. Formalin, which is an aqueous solution of formaldehyde, is usually used as formaldehyde.

Other monomer may be included to form the melamine foam. Such monomers include aldehydes such as acetaldehyde, trimethylol acetaldehyde, acrolein, benzaldehyde, furfurol, glyoxal, phthalaldehyde, terephthalaldehyde; C1-5 alkyl-substituted melamines such as methylolmelamine; methylmethylolmelamine and methylbutylolmelamine; urea; urethane; carbonic acid amides; dicyandiamide; guanidine; sulfurylamides; sulphonic acid amides; aliphatic amines; phenols and the derivatives thereof. The blowing agent may be pentane, trichlorofluoromethane, trichlorotrifluoroethane, etc. As the catalyst, formic acid is commonly used and, as the emulsifier, anionic surfactants such as sodium sulfonate may be used. The melamine foam may be reduced according to techniques described above. Additional description of melamine foam formation is provided in US Patent Application Publication Nos. 2010/0081604, 2010/0081605, and 2010/0081606.

The abrasive particles have a unique shape. The shape of the abrasive cleaning particle can be defined in various ways. The abrasive particles may have one or more of the following distinct particle parameters. Particle parameters include form factor, tip radius circularity, mean particle size, solidity, roughness, packing density, and hardness. Recent analytical techniques allow an accurate simultaneous measurement of particle shapes from a large number of particles, typically greater than 10,000 particles (however greater sampling sizes are envisioned such as above about 50,000 particles or about 100,000 particles). This enables accurate tuning and/or selection of average particle population shape with discriminative performance. Many of the measurement analyses of particle shape may be conducted using on Occhio Nano 500 Particle Characterisation Instrument with its accompanying software Callistro version 25 (Occhio s.a. Liege, Belgium). This instrument is used to prepare, disperse, image and analyse the particle samples, as per manufacturer's instructions, and the following instrument setting selections: White Requested=180, vacuum time=5000 ms, sedimentation time=5000 ms, automatic threshold, number of particles counted/analyses=8000 to 500000, minimum number of replicates/sample=3, lens setting 1×/1.5×.

Particle Size—The abrasive particles have a size defined by their area-equivalent diameter (ISO 9276-6:2008(E) section 7) also called Equivalent Circle Diameter ECD (ASTM F1877-05 Section 11.3.2). The mean ECD of particle population is calculated as the average of respective ECDs of each particle (excluding particles having ECD of below 10 microns) of a particle population of at least 10,000 particles; however greater sampling sizes are envisioned such as above about 50,000 particles or about 100,000 particles. Mean data are extracted from volume-based vs. number-based measurements. The abrasive particles have a mean ECD from 10 µm, 50 µm, 75 µm, or 100 µm to 1000 µm, 500 µm, 350 µm, or 250 µm. In a certain embodiment, the abrasive particles have a mean ECD of about 100 µm to about 250 µm.

Circularity—The abrasive particles may be non-rolling. By non-rolling, it is meant that the abrasive particle slide across the target surface (e.g., skin) rather than roll across the surface. It is believed that this non-rolling character promotes improved cleansing efficacy and exfoliation benefits. Circularity is a quantitative, 2-dimension image analysis shape description as measured according to ISO 9276-6:2008(E) section 8.2 as implemented via the Occhio Nano 500 Particle Characterisation Instrument with its accompanying software Callistro version 25 (Occhio s.a. Liege, Belgium). Circularity is a preferred mesoshape descriptor and is widely available in shape analysis instrument such as in Occhio Nano 500 or in Malvern Morphologi G3. Circularity is sometimes described in literature as being the difference between a particle's shape and a perfect sphere. Circularity values range from 0 to 1, where a circularity of 1 describes a perfectly spherical particles or disc particle as measured in a two dimensional image. Circularity is calculated by the following equation:

$$C = \sqrt{\frac{4\pi A}{P^2}}$$

wherein A is projection area, which is a 2D descriptor, and P is the perimeter length of the particle.

Abrasive particles may have a mean circularity from about 0.10, 0.15, 0.20, 0.30, or 0.35 to about 0.50, 0.45, or 0.40. In a certain embodiment, the abrasive particles have a mean circularity of about 0.35 to about 0.45. Mean data are extracted from volume-based vs. number-based measurements. By the term "mean circularity", it is meant the average of the circularity values of each particle (excluding particles having an ECD of below 10 microns) taken from a population of at least about 10,000 particles; however greater sampling sizes are envisioned such as above about 50,000 particles or about 100,000 particles.

Solidity—The abrasive particles may have a defined solidity. Solidity is a quantitative, 2-dimensional image analysis shape description, and is being measured according to ISO 9276-6:2008(E) section 8.2 as implemented via the Occhio Nano 500 Particle Characterisation Instrument with its accompanying software Callistro version 25 (Occhio s.a. Liege, Belgium). The abrasive particles may have at least one edge or surface having a concave curvature. Solidity is a mesoshape parameter, which describes the overall concavity of a particle/particle population. Solidity values range from 0 to 1, where a solidity number of 1 describes a non-concave particle, as measured in literature as being:

Solidity=$A/A_c$ wherein A is the area of the particle and Ac is the area of the convex hull (envelope) bounding the particle (i.e., area of the shaped defined by an imaginary elastic band about the particle). FIG. 1 depicts a particle (2) showing a convex hull (4).

Solidity is sometime also named "Convexity" in literature and in some apparatus software. However, convexity is defined in ISO 9276-6 as convexity=Pc/P where P is the length of the perimeter of the particle and Pc is length of the perimeter of the convex hull (envelope) bounding the particle). Despite solidity and convexity being similar mesoshape descriptors, the solidity measure expressed above by the Occhio Nano 500 (i.e., Solidity=A/Ac) is used herein.

The abrasive particles having a mean solidity from 0.40, 0.50, 0.60, 0.70, or 0.75 to 0.90, or 0.85. In a certain embodiment, the abrasive particles have a mean solidity of about 0.75 to about 0.85 or 0.90. Mean data are extracted from volume-based vs. number-based measurements. By the term "mean solidity", it is meant that the average of the solidity values of each particle (excluding particles having an ECD of below 10 microns) taken from a population of at least about 10,000 particles; however greater sampling sizes are envisioned such as above about 50,000 particles or about 100,000 particles.

Figures 2A, 2B, 2C:
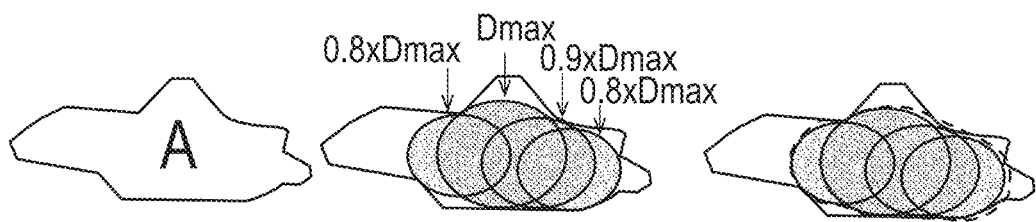
FIG. 2A is an illustration of a particle with an area.
FIG. 2B is an illustration of the particle of FIG. 2a with inscribed discs.
FIG. 2C is an illustration of the particle of FIG. 2a with showing the A(0.8).

Roughness—Roughness is a quantitative, 2-dimensional image analysis shape description, and is being measured according to ISO 9276-6:2008(E) section 8.2 as implemented via the Occhio Nano 500 Particle Characterisation Instrument with its accompanying software Callistro version 25 (Occhio s.a. Liege, Belgium). Roughness defines, in 2D measurement, the equivalent useful surface area outside of the core surface area of the particles and ranges from 0 to 1. A Roughness of 0 describes a particle with no useful mass available at the periphery of the core particle mass. Roughness is calculated as follows:

$$Rg\gamma = (A - A(O\gamma))/A$$

wherein A is the area of the particle and $A(O\gamma)$ is the surface area of what is considered the "core of the particle". $A-A(O\gamma)$ represent the "useful area at the periphery of the particle and the Roughness represents the fraction of that useful area vs. the total particle area. $O\gamma$ is called the tuneable tolerance factor and is typically set at 0.8, therefore the Roughness definition is $Rg\gamma = (A-A(0.8))/A$. In order to calculate the A(0.8), the maximum amount of discs are inscribed within the particle contour at each point of the particle's edge. The size, e.g.: area of the discs (circles) inscribed is defined by the Discs' diameters whereas the diameter value ranges between 0.8×Dmax and Dmax (where Dmax is the diameter value of the biggest disc inscribed in the particle). The core area of the particle A(0.8) is defined by the area corresponding to the projection of all the inscribed discs. FIGS. 2a-c depict how to calculate Roughness from the particle. FIG. 2A depicts a particle with an Area (A). FIG. 2B depicts the same particle with inscribed discs (circles) with various Diameters (D) include a disk with a maximum diameter (Dmax), a disc with a diameter 90% of the maximum diameter (0.9×Dmax), and two discs with a diameter 80% of the maximum diameter (0.8×Dmax). FIG. 2C depicts the particle with A(0.8) area corresponding to the projection of all the inscribed discs that have a diameter at least 80% of the disk with the maximum diameter.

Roughness is useful in abrasive particles since the non-spherical particles should have significant mass of material available at the periphery of its core. This peripheral mass is useful for cleaning performance and also for preventing the particle from rolling.

The abrasive cleaning particles may have a mean roughness from 0.05, 0.10, or 0.15 to about to 0.30, 0.28, 0.25, 0.20, or 0.15. In a certain embodiment, the abrasive particles have a mean roughness of about 0.05 to about 0.15. Mean data are extracted from volume-based vs. number-based measurements. By the term "mean roughness", it is meant that the average of the roughness values of each particle (excluding particles having an ECD of below 10 microns) taken from a population of at least about 10,000 particles; however greater sampling sizes are envisioned such as above about 50,000 particles or about 100,000 particles.

Form Factor—The abrasive particles are non-spherical. Subjectively, non-spherical means having a shape different from a sphere. More quantitatively, non-spherical means having a Form Factor (FF) of below about 0.75, 0.60, or about 0.50. Form Factor (FF) is a dimensional indicator that defines how a given particle is different from a regular form of a sphere especially emphasizing irregular surface topology (e.g., surface roughness) as defined by ASTM F1877-05 (June 2009) chapter 11.3.6, wherein:

$$FF = (4 \times \pi \times \text{Surface Area})/(\text{Perimeter})^2$$

wherein "Surface Area" meaning the surface area (in $\mu m^2$) of a particle and "Perimeter" the distance (in $\mu m$) around the cross-section of the particle that contains the longest axis.

Figures 3A, 3B:
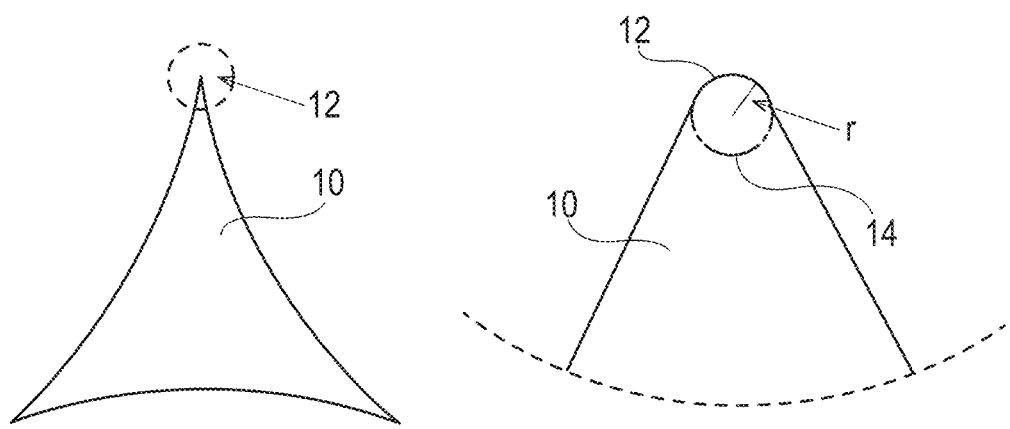

Edge Tip Radius—The abrasive particles in certain embodiments have sharp edges. FIG. 3A depicts an abrasive particle (10) with an edge (12). The area defined by the dashed circle is magnified in FIG. 3B. The sharpness of a particle edge (12) is defined by the edge having an edge tip radius (r). The edge tip radius (r) is defined by the radius of an imaginary circle (14) fitting the curvature of the edge extremity. The abrasive particle may have an edge tip radius of below about 8 $\mu m$, about 5 $\mu m$, or about 3 $\mu m$.

Packing Density—The abrasive cleaning particles may have a prescribed packing density. Packing density incorporates intrinsic information of the abrasive particles, which are otherwise known to have an impact on the cleaning performance, such as particle size and particle shape. Packing density also includes mass-efficient information taking into account the density of the raw material of the particle. Abrasive particles with too high of a packing density may have low cleaning performance while abrasive particles with too low of a packing density may have intrinsic fragility inadequate for cleaning purpose via mechanical abrasion. The abrasive particles may have a packing density ranging from 10, 50, 60, or 70 $kg/m^3$ to 250, 150, 120, or 100 $kg/m^3$. In a certain embodiment, the abrasive particles have a packing density of about 70 $kg/m^3$ to about 100 $kg/m^3$.

Packing density is calculated as follows. One tenth of a gram (0.1 g+/−0.001 g) of dry particles is placed into a 20 ml precise metric graduated Pyrex® volumetric cylinder (as available from Sigma-Aldrich). The cylinder is sealed (e.g. with a stopper or film), and subsequently shaken using a Vortex mixer (for example, the model L-46 Power Mix from Labinco DNTE SP-016) at 2500 rpm (maximum speed) for 30 seconds. The volume of the particles is measured after vibration. If the volume is between 5 to 15 ml, this is converted accordingly into packing density as expressed in $kg/m^3$. If the volume of 0.1 g is less than 5 ml, then two tenths of a gram (0.2 g+/−0.001 g) of dry particles is used to re-run the test in clean cylinder. If the volume of the 0.2 g is less than 5 ml, then half a gram (0.5 g+/−0.001 g) of dry particles is used to re-run the test in a clean cylinder. If the volume of the 0.5 g is less than 5 ml, then one gram (1.0 g+/−0.001 g) of dry particles is used to re-run the test in a clean cylinder, with volumes between 3 to 15 ml converted into $kg/m^3$ for packing density.

Hardness—The abrasive particles should be hard enough to provide good cleaning/cleansing performance while providing good surface safety and/or skin feel acceptability. The abrasive particles in the present invention may have hardness from 3, 4, 5, 10, or 15 $kg/mm^2$ to 50, 25, 20, or 15 $kg/mm^2$ according to HV Vickers hardness. In a certain embodiment, the abrasive particles have a hardness of about 15 to about 25 $kg/mm^2$.

Hardness is calculated as follows. Vickers hardness HV is measured at 23° C. according to standard methods ISO 14577-1, ISO 14577-2, ISO 14577-3. The Vickers hardness is measured from a solid block of the raw material at least 2 mm in thickness. In other words, hardness is measure of the precursor material before reduction (e.g., cutting, grinding, milling) to particles. The Vickers hardness micro indentation measurement is carried out by using the Micro-Hardness Tester (MHT), manufactured by CSM Instruments SA, Peseux, Switzerland, using the general settings as follows: Control mode=Displacement, Continuous; Maximum displacement=200 $\mu m$; Approach speed=20 nm/s; Zero point determination=at contact; Hold period to measure thermal drift at contact=60 s; Force application time=30 s; Frequency of data logging=at least every second; Hold time at maximum force=30 s; Force removal time=30 s; and Shape/Material of intender tip=Vickers Pyramid Shape/Diamond Tip.

As per the ISO 14577 instructions, the test surface should be flat and smooth, having a roughness (Ra) value less than 5% of the maximum indenter penetration depth. For a 200 µm maximum depth this equates to a Ra value less than 10 µm. As per ISO 14577, such a surface may be prepared by any suitable means, which may include cutting the block of test material with a new sharp microtome or scalpel blade, grinding, polishing or by casting melted material onto a flat, smooth casting form and allowing it to thoroughly solidify prior testing.

Alternatively, the abrasive cleaning particles in the present invention hardness may also be expressed according to the MOHS hardness scale. The abrasive cleaning particles may have a MOHS hardness is between 0.5 and 3.5 or between 1 and 3. The MOHS hardness scale is an internationally recognized scale for measuring the hardness of a compound versus a compound of known hardness, see Encyclopedia of Chemical Technology, Kirk-Othmer, 4th Edition Vol 1, page 18 or Lide, D. R (ed) CRC Handbook of Chemistry and Physics, 73 rd edition, Boca Raton, Fla.: The Rubber Company, 1992-1993. Many MOHS Test kits are commercially available containing material with known MOHS hardness. For measurement and selection of abrasive material with selected MOHS hardness, it is recommended to execute the MOHS hardness measurement with un-shaped particles e.g.: with spherical or granular forms of the abrasive material since MOHS measurement of shape particles will provide erroneous results.

Personal Care Composition

The personal care composition may comprise the aforementioned abrasive particles or combinations of said particles. The personal care composition may comprise from 0.1%, 0.3%, 0.5%, or 1% to 20%, 10%, 7%, or 4%, by weight of the total composition, of said abrasive particles.

The personal care composition may be a skin care, anti-perspirant, deodorant, cosmetic, or hair care product. The personal care composition may be used as, for example, a moisturizer, conditioner, anti-aging compound, skin lightener, sunscreen, sunless tanner, shave preparation, lipstick, foundation, mascara, after-shave, and combinations thereof. In certain embodiments, the composition is applied to the face, neck, hands, arms, and other typically exposed areas of the body.

The personal care composition may involve a wide variety of forms. Non-limiting examples include simple solutions (e.g., water or oil based), dispersions, and emulsions. The personal care composition may be substantially anhydrous. "Substantially anhydrous" means that the composition comprises no more than about 1%, 0.5%, or, 0% water. The personal care compositions may be fluid or solid (gels, sticks, flowable solids, amorphous materials). In certain embodiments, the personal care composition is in the form of an emulsion. Emulsion may be generally classified as having a continuous aqueous phase (e.g., oil-in-water and water-in-oil-in-water) or a continuous oil phase (e.g., water-in-oil and oil-in-water-in-oil).

In certain embodiment, the personal care composition has a turbidity of from about 5 NTU to less than about 3000 NTU, 1000 NTU, 500 NTU, or 100 NTU.

In select embodiments, the personal care composition may be in a form comprising at least one discrete, visually distinct first phase and at least one discrete, visually distinct second phase. For purposes of these select embodiments, "visually distinct" means that the phases can be separately seen by the human eye as distinctly separate regions (i.e., not emulsions or dispersions of particles. In one embodiment, at least one phase forms a stable pattern, for example a continuous or discontinuous line, a spiral, a curve, or other geometric shape, within a transparent phase, where "within" means that one phase is substantially surrounded by the other phase the and does not contact the side of a container. Alternatively, the phases may form a swirled pattern, wherein both phases alternately contact the side of a container and wherein the width of each of phase, when viewed through the side of a transparent container, is substantially constant, but may differ from each other. Alternatively, the phases may form a marbled pattern, wherein the phases alternately contact the side of the container and wherein the width of the individual phases, when viewed through the side of a transparent container, may vary throughout the composition. In one embodiment, the first phase is a transparent, clear or translucent aqueous phase and the second phase is either an opaque white or colored non-aqueous phase. In another alternative embodiment, at least one aqueous phase forms a pattern within a non-aqueous phase. It is recognized that the composition optionally may comprise a three or more visually distinct and stable phases. Discrete, visually distinct multi-phase compositions are described in U.S. Patent Application Publication Nos. 2007/0297996, 2004/0057920, and 2004/0219119.

Carriers

The personal care composition may comprise a carrier. Carriers may be selected for various stability, aesthetics, and/or compatibility with other materials present in the personal care composition.

Suitable carriers include water and/or water soluble solvents. The personal care composition may comprise from about 1% to about 95% by weight of water and/or water-equivalent solvent. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable water-equivalent solvents include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, decanediol; glycerin; water, and mixtures thereof. In certain embodiments, the personal care composition comprises water, diols, glycerin, and combinations thereof.

Suitable carriers also include oils. The personal care composition may comprise from about 1% to about 95% by weight of one or more oils. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% of one or more oils. Oils may be used to solubilize, disperse, or carry materials that are not suitable for water or water-equivalent solvents. Suitable oils include silicones, hydrocarbons, esters, fatty amides, ethers, and mixtures thereof. Oils may be fluid at room temperature. However, certain personal care product forms (i.e., solid or semi-solid stick) may require non-fluid oils. The oils may be volatile or nonvolatile. "Non-volatile" means a material that exhibits a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm. of mercury at 20° C. Volatile oils may be used to provide a lighter feel when a heavy, greasy film is undesirable.

Suitable oils include volatile oils. In certain embodiments, the volatile oils may have a viscosity ranging from about 0.5 to about 5 centistokes 25° C. Volatile oils may be used to promote more rapid drying of the skin care composition after it is applied to skin. Nonvolatile oils are also suitable for use in the composition. Nonvolatile oils are often used for emolliency and protective properties. Nonvolatile oils preferably may have a viscosity ranging from about 5 to about 800,000 cst (or greater) or from about 20 to about 200,000 cst.

Suitable silicone oils include polysiloxanes. Polysiloxanes may have a viscosity of from about 0.5 to about 1,000,000 centistokes at 25° C. Such polysiloxanes can be represented by the general chemical formula:

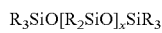

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

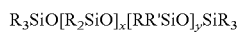

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as s 2502 Cosmetic Fluid from Dow Corning or as Abil Wax 9801 or 9814 from Evonik Goldschmidt GmbH.

Cyclic silicones are one type of silicone oil that may be used in the composition. Such silicones have the general formula:

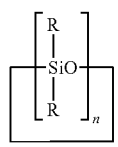

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Other silicone oils suitable for use in the personal care composition include polymers having the general formula:

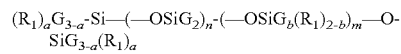

wherein G is hydrogen, phenyl, hydroxy, or $C_1$-$C_8$ alkyl, preferably methyl; a is a number 0-3; b is 0 or 1, preferably 1; n is a number from 0 to 1,999 (alternately, from 49 to 499); m is an integer from 1 to 2,000 (alternately, from 1 to 10); the sum of n and m is a number from 1 to 2,000 (alternately, from 50 to 500); $R_1$ is a monovalent radical conforming to the general formula $(CH_2)_qL$, wherein q is an integer having a value from 1 to 8 and L is selected from the following groups:

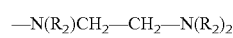

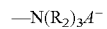

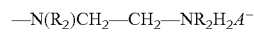

wherein $R_2$ is hydrogen, phenyl or aryl, or a saturated hydrocarbon radical, preferably an alkyl radical from about $C_1$ to about $C_{20}$, and A is a halide ion. An exemplary silicone polymer is trimethylsilylamodimethicone as shown in the following formula:

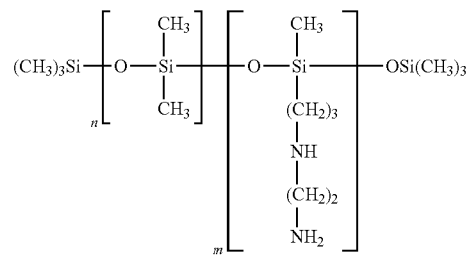

Another exemplary silicone polymer is represented by the general formula:

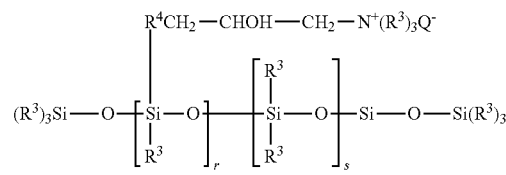

wherein $R^3$ is a monovalent hydrocarbon radical from $C_1$ to $C_{18}$, preferably an alkyl or alkenyl, such as methyl; $R_4$ is a hydrocarbon, preferably a $C_1$ to $C_{18}$ alkylene or a $C_{10}$ to $C_{18}$ alkyleneoxy, more preferably a $C_1$ to $C_8$ alkyleneoxy; $Q^-$ is a halide ion, preferably chloride; r is an average statistical value from 2 to 20, preferably from 2 to 8; s is an average statistical value from 20 to 200, preferably from 20 to 50. A suitable polymer of this class is known as UCARE SILICONE ALE 56™, available from Union Carbide. Other suitable silicone materials are disclosed in US Patent Application Publication No. 2007/0039103 A1.

Suitable hydrocarbon oils include straight or branched chain alkanes and alkenes. The chain length may be selected based on desired functional characteristics such as volatility. Suitable hydrocarbon oils may have between 5-20 carbon atoms or, alternately, between 8-16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105. Suitable hydrocarbons include isooctane, isododecane, isohexadecane, isoeicosane by Permethyl Corporation under the tradename Permethyl®. Suitable hydrocarbon oils may have greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof.

Other suitable oils include esters. Suitable esters typically contain at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate. Other suitable esters are further described in the Personal Care Product Council's *International Cosmetic Ingredient Dictionary and Handbook*, Thirteenth Edition, 2010, under the functional category of "Esters."

Other esters suitable for use in the personal care composition include mono-carboxylic acid esters of the general formula R'COOR, wherein R' and R are straight or branched chain, saturated or unsaturated alkyl, aryl, and wherein sum of carbon atoms in R' and R is at least 10, A suitable monoester is alkyl benzoate such as C12-15 alkyl benzoate.

Other esters suitable for use in the personal care composition include di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, dibutyl adipate, and tristearyl citrate.

Other esters suitable for use in the personal care composition include those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters.

Still other esters suitable for use in the personal care composition include glycerides, including, but not limited to, mono-, di-, and tri-glycerides. For use in the compositions described herein, the glycerides may be mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, sweet almond oil, apricot kernel oil, *camelina sativa* oil, rapeseed oil, tamanu seed oil, linseed oil, coconut oil, lanolin oil, soybean oil, and the like. Synthetic oils include, but are not limited to, triolein and tristearin glyceryl dilaurate. Other glyceryl esters of fatty acids include fatty acid mono-, di-, and triglycerides which are natural fats or oils that have been modified such as glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl disterate, glyceryl linoleate, glyceryl myristate, glyceryl isostearate, PEG castor oils, PEG glyceryl oleates, PEG glyceryl stearates, PEG glyceryl tallowates, and the like.

Other suitable oils include fatty amides. Fatty amides include compounds having an amide functional group while being liquid at 25° C. and insoluble in water. In certain embodiments, the fatty amide may have the general formula:

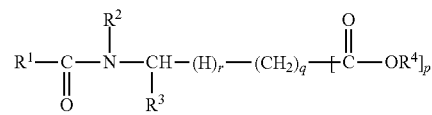

wherein R1 is an optionally functionalized, aliphatic, cycloaliphatic or cyclic, saturated or unsaturated, monovalent hydrocarbon radical containing from 1 to 30 carbon atoms (alternately, from 1 to 22 carbon atoms); R2, R3 and R4, which may be identical or different, are hydrogen or optionally functionalized, aliphatic, cycloaliphatic or cyclic, saturated or unsaturated, monovalent hydrocarbon radicals containing from 1 to 30 carbon atoms, preferably from 1 to 22 carbon atoms; r is 0 or 1; q is an integer from 0 to 2; and p equals 0 or 1. Particular fatty amides include N-acetyl-N-butylaminopropionate, isopropyl N-lauroylsarcosinate, and N,N,-diethyltoluamide. Other suitable fatty amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

Emulsifiers

The personal care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. Nos. 3,755,560, 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifying ethers and esters include:

Ethers of polyglycols and of fatty alcohols—including saturated or unsaturated $C_{12-30}$ alcohols (e.g., oleyl alcohol, cetyl alcohol, stearyl alcohol or behenyl alcohol) and polyglycols comprising n number of oxyalkylene groups wherein n=an integer from 1 to 200 or, alternately, from 2 to 30 (e.g., 1 to 20 oxyethylene groups). Particular examples include compounds with the INCI names of steareth-n, beheneth-n or oleth-n. Suitable examples include compounds having the INCI names steareth-8, steareth-10, steareth-16, steareth-20, ceteth-10, laureth-4, laureth-3, trideceth-6, ceteareth-5, oleth-10, and beneth-10.

Esters of polyglycols and of fatty acids—including saturated or unsaturated $C_{12-30}$ fatty acids (e.g., oleic acid, cetylic acid, stearic acid) and polyglycols comprising n number of oxyalkylene groups wherein n=an integer from 1 to 200 or alternately, 1 to 50 (e.g., 1 to 20 oxyethylene groups). Particular examples include compounds with the INCI name PEG-n stearate or PEG-n oleate). Suitable examples include polyethylene glycol-8 monostearate, polyethylene glycol-10, or polyethylene glycol-12 distearate.

Ethers of polyglycols and of fatty alcohols which are glycosylated—including $C_{12-30}$ alcohols having from 1 to 10 glycosyl groups and polyglycols comprising n number of oxyalkylene groups wherein n=an integer from 1 to 200 (e.g., 1 to 20 oxyethylene groups). A suitable example includes polyoxyethylenated (20 OE) methyl glucose distearate, Esters of polyglycols and of fatty acids which are glycosylated—including $C_{12-30}$ fatty acids having from 1 to 10 glycosyl groups and polyglycols comprising n number of oxyalkylene groups wherein n=an integer from 1 to 200 (e.g., 1 to 20 oxyethylene groups).

Ethers of $C_{12-30}$ alcohols and of glycerol or of polyglycerol—A suitable example includes polyglyceryl-3 cetyl ether, such as Chimexane NL from Chimex, Esters of C12-30 fatty acids and of glycerol or of polyglycerol—including esters comprising from 1 to 10 glycerol groups. Particular examples include hexa-glyceryl monosterate, diglyceryl distearate, tetraglyceryl tristearate, decaglyceryl decastearate, diglyceryl monostearate, hexaglyceryl tristearate, decaglyceryl pentastearate, the ester of glycerol and of palmitic and stearic acids, and glyceryl mono- and dibehenate.

Ethers of oxyalkylene-modified C12-30 alcohols and of glycerol or polyglycerol.

Ethers of $C_{12-30}$ fatty alcohols comprising and of sucrose or glucose—Suitable examples include compounds with the INCI names of C12-18 alkylglucoside, C12-20 alkylglucoside (e.g., Montanov L from Seppic), cetearyl glucoside (e.g., a mixture with cetearyl alcohol under the reference Montanov 68 from Seppic), myristyl glucoside (e.g., a mixture with myristyl alcohol under the reference Montanov 14 from Seppic) or cetearyl glucoside (e.g., Tegocare CG 90 from Evonik Goldschmidt), Esters of sucrose and of $C_{12-30}$ fatty acids—Particular examples include sucrose distearate or sucrose tristearate, sucrose cocoate, sucrose dilaurate, sucrose distearate, sucrose hexaerucate, sucrose hexapalmitate, sucrose laurate, sucrose mortierellate, sucrose myristate, sucrose oleate, sucrose palmitate, sucrose pentaerucate, sucrose polybehenate, sucrose polycottonseedate, sucrose polylaurate, sucrose polylinoleate, sucrose polyoleate, sucrose polypalmate, sucrose polysoyate, sucrose polystearate, sucrose ricinoleate, sucrose stearate, sucrose tetraisostearate, and sucrose trilaurate. A suitable example includes the mixture of esters (mono- and polyesters) of stearic acid and of sucrose sold as Crodesta Fl 10 by Croda.

Esters of pentaerythritol and of $C_{12-30}$ fatty acids—Particular examples include pentaerythritol tetrastearate.

Esters of sorbitol and/or of sorbitan and of $C_{12-30}$ fatty acids—Particular examples include sorbitan monostearate, sorbitan tristearate, or sorbitan laurate, such as Span 20 from Uniqema, Ethers of sorbitol and/or of sorbitan and of alkoxylated sorbitan—Suitable examples include sorbeth-8 beeswax or sorbeth-20 beeswax from Nikko Chemical.

Ethers of polyglycols and of cholesterol—Particular examples include choleth-3, choleth-10 (such as Emalex CS-10 from Nihon Emulsion Company), choleth-15 (such as Emalex CS-15 from Nihon Emulsion Company) or choleth-20 (such as Emalex CS-20 from Nihon Emulsion Company).

Esters of $C_{12-30}$ fatty acids and of alkoxylated ethers of sorbitol and/or of Suitable examples include polysorbate-60, polysorbate-61, sorbeth-3 isostearate, polyoxyethylenated 4 OE sorbitan monostearate, and polyoxyethylenated 20 OE sorbitan tristearate.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Exemplary materials include materials with the following International Nomenclature of Cosmetic Ingredients (INCI) designations: Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-IO Phosphate; Dimethicone PEG/PPG-7/4 Phosphate; Dimethicone PEG/PPG-12/4 Phosphate; Dimethicone PEG-7 Undecylenate; Lauryl Dimethicone PEG-IO Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG- 20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; and mixtures thereof.

Emulsifiers also include emulsifying silicone elastomers. Suitable emulsifying silicone elastomers may include at least one polyalkyl ether or polyglycerolated unit. These cross-linked elastomers may also be co-modified to include alkyl substituents. Suitable formation techniques are described in U.S. Pat. Nos. 5,236,986; 5,412,004; 5,837,793; and 5,811,487. Polyoxyalylenated emulsifying silicone elastomers that may be used in at least one embodiment of the invention include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011.

Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Another suitable crosslinked silicone elastomer emulsifier is dimethicone/PEG-10/15 crosspolymer, which provides excellent aesthetics due to its elastomeric backbone, but also excellent emulsification properties. Further examples of crosslinked organosiloxane emulsifiers include, but are not limited to dimethicone/dimethicone PEG/PPG 15 crosspolymer; dimethicone PEG-10 crosspolymer; dimethicone PEG-10/15 crosspolymer; dimethicone PEG-15 crosspolymer; dimethicone polyglycerin-3 crosspolymer; dimethicone PPG-20 crosspolymer; lauryl dimethicone PEG-15 crosspolymer; lauryl dimethicone polyglycerin-3 crosspolymer; PEG-8 dimethicone polysorbate-20 crosspolymer; PEG-10 dimethicone/vinyl dimethicone crosspolymer; PEG-10 lauryl dimethicone crosspolymer; PEG-15/lauryl dimethicone crosspolymer; PEG-15 laurylpolydimethylsiloxy ethyl crosspolymer; and mixtures thereof.

It should be recognized that silicone elastomers may be supplied pre-swollen with a solvent. With a pre-swollen swollen elastomer, the weight percentages recited for emulsifier use (i.e., from about 0.05% to about 20%, from about 0.1% to about 10%, from about 0.5% to about 5%, or from about 1% to about 3% emulsifier) are of the elastomer alone (i.e., excluding the weight of the solvent).

Structuring Agent

The personal care composition may comprise a structuring agent. Structuring agents may be used to increase viscosity, thicken, solidify, or provide solid or crystalline structure to the personal care composition. The structuring agent may be used to suspend or disperse the abrasive particles. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents.

Polysaccharides and gums may be used as aqueous phase thickening agents. Examples of such polysaccharides and gums include naturally derived materials such as agar, agarose, alicaligenes polysaccharides, algin, alginic acid, *acacia* gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, ammonium alginate, calcium alginate, calcium carrageenan, carnitine, carrageenan, guar gum, guar hydroxypropyltrimonium chloride, hyaluroinic acid, hydroxypropyl chitosan, hydroxypropyl guar, karaya gum, kelp, locust bean gum, natto gum, potassium alginate, potassium carrageenan, propylene glycol alginate, sodium carboyxmethyl dextran, sodium carrageenan, tragacanth gum, and mixtures thereof. Suitable polysaccharides include alkyl hydroxyalkyl cellulose ethers such as cetyl hydroxyethylcellulose, which is the ether of cetyl alcohol and hydroxyethylcellulose. This material is sold under the tradename Natrosol® Plus CS from Ashland Aqualon Functional Ingredients. Other useful polysaccharides include scleroglucans comprising a linear chain of (1-3) linked glucose units with a (1-6) linked glucose every three units, a commercially available example of which is Clearogel™ CS 11 from M.M.P., Inc.

Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof.

Carboxylic acid polymers include carbomers. These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Suitable materials includes include the Carbopol® 900 series (e.g., Carbopol® 945, Carbopol® 940, Carbopol® 950, Carbopol® 954, Carbopol® 980, Carbopol® 951 and Carbopol® 981 from Noveon, Inc) and the Carbopol® Ultrez series (e.g., Carbopol® Ultrez 10 polymer, Carbopol® Ultrez 20 polymer, and Carbopol® Ultrez 21 polymer). Other suitable carboxylic acid polymeric agents include copolymers of $C_{10-30}$ alkyl acrylates with one or more monomers of acrylic acid, methacrylic acid, or one of their short chain (i.e., $C_1$-4 alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, PEMULEN™ TR-1, and PEMULEN™ TR-2, from Noveon, Inc.

Sulfonated polymers include polymers and copolymers containing 2-acrylamido-2-methylpropane sulfonic acid (i.e., AMPS or acryloyldimethyl tauric acid) and salts thereof. Exemplary AMPS structurants include sodium acrylate/sodium acryloyldimethyl taurate copolymer available as SIMULGEL® EG and SIMULGEL® EPG or hydroxyethyl acrylate/sodium acryloyldimethyl taurate copolymer available as SIMULGEL® NS, SIMULGEL® FL, and SIMULGEL® I-NS 100; which are available from Seppic Corporation (Fairfield, N.J.). Another suitable sulfonated polymer is sodium polyacryloyldimethyl taurate available as Simulgel® 800 from Seppic Corporation (Fairfield, N.J.). Other suitable sulfonated polymers include acrylamide/sodium acryloyldimethyltaurate/acrylic acid copolymer available as Acudyne™ SCP from Rohm and Haas Company, Inc.; acrylamide/sodium acryloyldimethyltaurate copolymer available as Simulgel® 600 from Seppic; ammonium acryloyldimethyltaurate/beheneth-25 methacrylate crosspolymer avilable as Aristoflex® BLV from Clariant International Ltd.; ammonium acryloyl dimethyltaurate/carboxyethyl acrylate crosspolymer avilable as Aristoflex® TAC from Clariant International Ltd.; ammonium acryloyldimethyltaurate/vinylpyrrolidone copolymer available as Aristoflex® AVC from Clariant International Ltd.; dimethylacrylamide/sodium acryloyldimethyltaurate crosspolymer available as SUpolymer G-1 from Toho Chemical Industry Co., Ltd.; sodium acrylate/acryloyldimethyltaurate/dimethylacrylamide crosspolymer available as Sepinov™ P88 from Seppic; and sodium acryloyldimethyltaurate/VP Crosspolymer available as Aristoflex® AVS from Clariant International, Ltd. Additional sulfonated structurants are described in US Patent Application Publication Nos. 2007/0140993 (identified as gelling agent in the form of a copolymer of acryloyl dimethyl tauric acid or a salt thereof) and 2006/0147396 A1 (identified as "polymer containing at least one sulphofunctional monomer").

Acrylamide polymers and copolymers include SEPIGEL® 305 from Seppic Corporation (Fairfield, N.J.), which is designated by the Personal Care Product Council's *International Cosmetic Ingredient Dictionary and Handbook*, Thirteenth Edition, 2010, as "polyacrylamide and isoparaffin and laureth-7." Other polyacrylamide polymers include multi-block copolymers of acrylamides and substituted acrylamides with acrylic acids and substituted acrylic acids. Commercially available examples of these multi-block copolymers include HYPAN® SR150H, SS500V, SS500 W, SSSA100H, from Lipo Chemicals, Inc., (Patterson, N.J.).

High molecular weight polyalkylglycols or polyglycerins may be used as structuring agents. Suitable materials include polyethylene glycols (PEG) derivatives and polypropylene glycols (PPG) derivatives with an n degree of polymerization. n may be from 50 to 200,000. Other suitable materials are polyglycerins having repeating glycerin moieties where the number of repeating moieties ranges from about 15 to about 200, or from about 20 to about 100. Examples of suitable polyglycerins include those having the INCI names polyglycerin-20, polyglycerin-40, and the like.

Examples of oil structuring agents include silicone and organic based materials. Suitable ranges of oil structuring agents are from about 0.01%, 0.05%, 0.1% 0.5%, 1%, 2.5%, 5%, or 10% to about 30%, 25%, 20%, 15%, 10%, or 5%. Suitable oil phase structuring agents may be silicone based, such as silicone elastomers, silicone gums, silicone waxes, linear silicones having a degree of polymerization allowing the silicone to increase the viscosity of the oil phase. Examples of silicone structuring agents include, but are not limited to, silicone elastomers, silicone gums, and silicone waxes.

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst. Cross-linked organopolysiloxane elastomers useful in the present invention and processes for making them are further described in U.S. Pat. Nos. 4,970,252, 5,760,116, and 5,654,362, 6,524,598, and 6,696,049. It is particularly desirable to incorporate silicone elastomers into the compositions of the invention because they provide excellent "feel" to the composition, are very stable in cosmetic formulations, and relatively inexpensive.

Suitable silicone elastomers may be in the powder form, or dispersed or solubilized in solvents such as volatile or nonvolatile silicones, or silicone compatible vehicles such as hydrocarbons or esters. Examples of silicone elastomer powders include vinyl dimethicone/methicone silesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluorosilicone elastomer, and hybrid silicone powders that contain a phenyl group such as KSP-300, available from Shin-Etsu, which is a phenyl substituted silicone elastomer; and DC 9506 available from Dow Corning.

Examples of silicone elastomer dispersed in a silicone compatible vehicle include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crosspolymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44.

Silicone gums are another oil phase structuring agent. The silicone gum typically has a viscosity ranging from about 500,000 to 100 million cst at 25° C., from about 600,000 to 20 million, from about 600,000 to 12 million cst. The silicone gums that are used in the compositions include, but are not limited to, those of the general formula wherein:

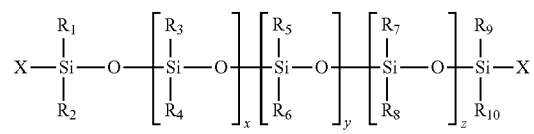

$R_1$ to $R_{10}$ are each independently hydrogen, an alkyl having 1 to 30 carbon atoms, aryl, or aralkyl; and X is H, OH, or a C1-30 alkyl or vinyl. x, y, or z may be zero with the proviso that $(x+y+z) \geq 1$.

Such silicone gums may be purchased in pure form from a variety of silicone manufacturers including Wacker-Chemie or Dow Corning, and the like. Silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1-1254 Fluid, 2-9023 Fluid, and 2-9026 Fluid. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone. Another example is a mixture of dimethiconol and volatile or nonvolatile silicone available from the Dow Corning Corporation as tradename 1401 Fluid, 1403 Fluid, and 1501 Fluid.

Another type of oily phase structuring agent includes silicone waxes. Silicone waxes may be referred to as alkyl silicone waxes which and are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable structuring agents include polyamides and polysilicone-polyamide copolymers. Suitable polysilicone-polyamide copolymers are disclosed in U.S. Patent Application Publication No. 2004/0170586. A specific example of such copolymers is nylon 611/dimethicone copolymers by Dow Corning under the tradename Dow Corning 2-8178. Also suitable are polyamides such as those purchased from Arizona Chemical under the Uniclear™ and Sylvaclear® including Sylvaclear® A200V or A2614V (INCI name: ethylenediamine/hydrogenated dimer dilinoleate copolymer/bis-di-C14-18 alkyl amide); Sylvaclear® AF1900V and Sylvaclear® PA1200V (INCI name: Polyamide-3); Sylvaclear® C75V (INCI name: bis-stearyl ethylenediamine/neopentyl glycol/stearyl hydrogenated dimer dilinoleate copolymer); Sylvaclear® PE400V (INCI name: Polyamide-6); Sylvaclear® WF 1500V (INCI name: Polyamide-4); or Uniclear™ 100 VG (INCI name: ethylenediamine/stearyl dimer dilinoleate copolymer; or ethylenediamine/stearyl dimer ditallate copolymer).

Other oil phase structuring agents may include one or more natural or synthetic waxes such as animal, vegetable, or mineral waxes. Generally such waxes have a melting point ranging from about 25° C. to 125° C., and alternatively from about 30° C. to about 100° C. Non-limiting examples of suitable waxes include silicone waxes, fatty esters, for example cetyl and/or stearyl esters, *acacia*, beeswax, ceresin, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, candelilla, grape wax, polyalkylene glycol derivatives thereof (for example PEG6-20 beeswax, or PEG-12 carnauba wax) and mixtures of any of the aforementioned waxes. In one embodiment, the wax is a polyethylene wax, and alternatively is a polyethylene wax having a melting point of less than 120° C., alternatively less than 95 C, and alternatively less than 85° C.

Non-limiting examples of suitable silicone waxes are disclosed in U.S. Pat. Nos. 5,413,781 and 5,725,845, and further include alkylmethyl polysiloxanes, C10-C60 alkyl dimethicones, and mixtures thereof. Alternatively, the silicone wax may be a C16-C28 alkyl dimethicone wax. Other suitable silicone waxes include, but are not limited to stearoxydimethicone, behenoxy dimethicone, stearyl dimethicone, cetearyl dimethicone, cetyl dimethicone, and mixtures thereof.

Other structuring agents are natural or synthetic montmorillonite minerals such as hectorite, bentonite, and quaternized derivatives thereof, which are obtained by reacting the minerals with a quaternary ammonium compound (e.g., stearalkonium bentonite and stearalkonium hectorite).

Other structuring agents are silicas, silicates, silica sylylate, and alkali metal or alkaline earth metal derivatives thereof. These silicas and silicates are generally found in the particulate form and include silica, silica silylate, magnesium aluminum silicate, and the like.

Optional Personal Care Ingredients

The personal care compositions may comprise one or more optional components to provide an efficacious and/or consumer desirable product. For example, the composition can include other actives or agents. For instance, suitable optional actives and agents may include an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, particulate materials, UV actives, photostabilizers, anti-cellulite agents, desquamation actives, anti-acne actives, anti-oxidants, radical scavengers, conditioning agents, anti-inflammatory agents, tanning actives, skin lightening agents, botanical extracts, antimicrobial actives, antifungal actives, antibacterial actives, antiperspirant actives, sensates, preservatives, anti-dandruff actives, substantivity polymers, detersive surfactants, and combinations thereof. Suitable optional components are discussed in more detail below.

1. Sugar Amines

The compositions of the present invention can comprise a sugar amine, which is also known as amino sugar. Sugar amine compounds useful in the present invention can include those described in PCT Publication WO 02/076423 and U.S. Pat. No. 6,159,485. In one embodiment, the composition may comprise from about 0.001%, 0.01%, 0.05%, 0.1%, 0.5%, or 1% to about 10%, 7, 5%, or 2% by weight of the composition, of one or more sugar amine.

Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, "sugar amine" includes isomers and tautomers of such and its salts (e.g., HCl salt) and is commercially available from Sigma Chemical Co.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine.

2. Vitamins

In one embodiment, the composition may comprise from about 0.001%, 0.01%, 0.05%, 0.1%, 0.5%, or 1% to about 10%, 7, 5%, or 2%, by weight of the composition, of one or more vitamins. "Vitamins" means vitamins, pro-vitamins, and their salts, isomers and derivatives. Non-limiting examples of suitable vitamins include: vitamin B compounds (including B1 compounds, B2 compounds, B3 compound, B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids.

In certain embodiments, the personal care compositions comprise a vitamin B3 compound. Vitamin B3 compounds are particularly useful for regulating skin conditions, as described in U.S. Pat. No. 5,939,082. In one embodiment, the composition may comprise from about 0.001%, 0.01%, 0.05%, 0.1%, 0.5%, or 1% to about 50%, 20%, 10%, 7%, or 5%, by weight of the composition, of the vitamin B3 compound.

As used herein, "vitamin B3 compound" means a compound having the formula:

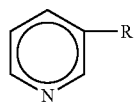

wherein R is —$CONH_2$ (i.e., niacinamide), —COOH (i.e., nicotinic acid) or —CH2OH (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g., tocopherol nicotinate, myristyl nicotinate), nicotinyl amino acids, nicotinyl alcohol esters of carboxylic acids, nicotinic acid N-oxide and niacinamide N-oxide.

3. Oil Control Agents

The personal care compositions may comprise one or more oil control agents for regulating the production of skin oil, sebum, or for improving the appearance of oily skin. Examples of suitable oil control agents include salicylic acid, dehydroacetic acid, benzoyl peroxide, vitamin B3 compounds, their isomers, esters, salts and derivatives, and mixtures thereof. Dehydroacetic acid includes materials having the formula:

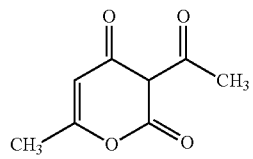

or dermatologically acceptable salts, derivatives or tautomers thereof. The technical name for dehydroacetic acid is 3-Acetyl-6-methyl-2H-pyran-2,4(3H)-dione and can be commercially purchased from Lonza.

Dermatologically acceptable salts include alkali metal salts, such as sodium and potassium; alkaline earth metal salts, such as calcium and magnesium; non-toxic heavy metal salts; ammonium salts; and trialkylammonium salts, such as trimethylammonium and triethylammonium. In particular embodiments, sodium, potassium, and ammonium salts of dehydroacetic acid may be used. Sodium dehydroacetate is available from Tri-K Industries, Inc., as Tristat SDHA. Derivatives of dehydroacetic acid include, but are not limited to, any compounds wherein the $CH_3$ groups are individually or in combination replaced by amides, esters, amino groups, alkyls, and alcohol esters. Tautomers of dehydroacetic acid are the isomers of dehydroacetic acid which can change into one another with great ease so that they ordinarily exist in equilibrium. Thus, tautomers of dehydroacetic acid can be described as having the chemical formula $C_8H_8O_4$ and generally having the formula above.

Other oil control agents include materials capable of absorbing oils and sebum. Suitable oil absorbing materials include starch, calcium silicate, polyethylene, nylon, boran nitride, mica, clays such as bentonite, montmarrillonite and kaolin, zeolite, cyclodextrins, fumed silica, synthetic clays such as polymer powders including natural, synthetic, and semisynthetic cellulose, fluorocarbon resins, polypropylene, modified starches of cellulose acetate, particulate cross-linked hydrophobic acrylate or methacrylate copolymers and mixtures thereof.

In one embodiment, the personal care composition may comprise from about 0.001%, 0.01%, 0.05%, 0.1%, 0.5%, or 1% to about 25%, 20%, 10%, 7%, 5%, or 3% by weight of the composition, of one or more oil control agents.

4. Phytosterols

The personal care compositions may comprise a phytosterol. For example, one or more phytosterols can be selected from the group consisting of β-sitosterol, campesterol, brassicasterol, A5-avennasterol, lupenol, α-spinasterol, stigmasterol, their derivatives, analogs, and combinations thereof. In certain embodiments, the phytosterol is selected from the group consisting of β-sitosterol, campesterol, brassicasterol, stigmasterol, their derivatives, and combinations thereof. In a select embodiment, the phytosterol is stigmasterol.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company, Sigma Chemical Company, and Cognis.

In one embodiment, the composition may comprise from about 0.0001%, 0.001%, 0.01%, 0.05%, 0.1%, 0.5%, or 1% to about 25%, 20%, 10%, 7%, 5%, or 3%, by weight of the composition, of one or more phytosterol.

5. Hexamidine Compounds

The personal care compositions may include hexamidine compounds, its salts, and derivatives. As used herein, "hexamidine compound" means a compound having the formula:

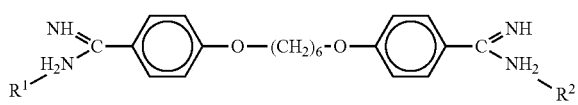

wherein $R^1$ and $R^2$ are optional or are organic acids (e.g., sulfonic acids, etc.).

In one embodiment, the composition may comprise from about 0.0001%, 0.001%, 0.01%, 0.05%, 0.1%, 0.5%, or 1% to about 25%, 20%, 10%, 7%, 5%, or 3%, by weight of the composition, of one or more hexamine compounds.

As used herein, hexamidine derivatives include any isomers and tautomers of hexamidine compounds including but not limited to organic acids and mineral acids, for example sulfonic acid, carboxylic acid, etc. In a select embodiment, the hexamidine compounds include hexamidine diisethionate, commercially available as Eleastab® HP100 from Laboratories Serobiologiques.

6. Tightening Agents

The personal care composition may comprise a tightening agent. A tightening agent is a compound capable of having a tightening effect on keratinous tissues and, typically, on skin. Suitable tightening agents may be chosen from plant or animal proteins and their hydrolysates such as maize, rye, wheat, buckwheat, sesame, spelt, pea, bean, lentil, soybean and lupin; polysaccharides of natural origin including (i) polyholosides, for example, in the form of starch derived especially from rice, maize, potato, cassava, peas, wheat, oats, etc. or in the form of carrageenans, alginates, agars, gellans, cellulose polymers and pectins, advantageously as an aqueous dispersion of gel microparticles, and (ii) latices composed of shellac resin, gum sandarac, dammars, elemis, copals, cellulose compounds, and mixtures thereof; mixed silicates including phyllosilicates and in particular laponites; colloidal particles of inorganic fillers such as silica/alumina colloidal particles such as those sold under then tradename LUDOX® by W.R. Grace & Co.; synthetic polymers such as polyurethane latices or acrylic/silicone latices, in particular those described in US Patent Application Publication No. 2002/0131948, including propylthio(polymethyl acrylate), propylthio(polymethyl methacrylate) and propylthio(polymethacrylic acid) grafted polydimethylsiloxane, propyl-thio (polyisobutyl methacrylate) and propylthio(poly-methacrylic acid) grafted polydimethylsiloxane (available under the tradenames VS 80, VS 70 and L021 from 3M); and mixtures thereof.

The personal care composition may comprise from about 0.0001%, 0.001%, 0.01%, 0.05%, 0.1%, 0.5%, or 1% to about 30%, 25%, 20%, 10%, 7%, 5%, or 3% by weight of the composition, of one or more tightening agent.

7. Anti-Wrinkle Actives/Anti-Atrophy Actives

The compositions of the present invention can comprise a one or more anti-wrinkle actives or anti-atrophy actives. Exemplary anti-wrinkle/anti-atrophy actives suitable for use in the compositions of the present invention include dialkanoyl hydroxyproline compounds, hydroxy acids (e.g., glycolic acid, lactic acid, lactobionic acid), keto acids (e.g., pyruvic acid), phytic acid, lysophosphatidic acid, stilbenes, cinnamates, resveratrol, kinetin, zeatin, dimethylaminoethanol, peptides from natural sources (e.g., soy peptides), and salts of sugar acids (e.g., Mn gluconate, Zn gluconate). In one embodiment, the composition may comprise from about 0.0001%, 0.001%, 0.01%, 0.05%, 0.1%, 0.5%, or 1% to about 30%, 25%, 20%, 10%, 7%, 5%, or 3% by weight of the composition, of one or more anti-wrinkle/anti-atrophy compounds.

Suitable dialkanoyl hydroxyproline compounds of the present invention can include those corresponding to the following chemical formula:

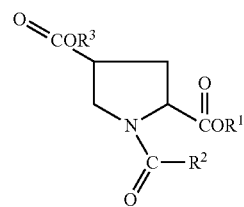

wherein $R^1$ is H, X, $C_1$-$C_{20}$ straight or branched alkyl,
X is metals (Na, K, Li, Mg, Ca) or amines (DEA, TEA);
$R^2$ is $C_1$-$C_{20}$ straight or branched alkyl;
$R^3$ is $C_1$-$C_{20}$ straight or branched alkyl.

Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalmitoyl hydroxyproline includes any isomers and tautomers of such and is commercially available under the tradename Sepilift DPHP® from Seppic, Inc. Further discussion of dipalmitoyl hydroxyproline appears in PCT Publication WO 93/23028. Preferably, the dipalmitoyl hydroxyproline is the triethanolamine salt of dipalmitoyl hydroxyproline as discussed in U.S. Pat. No. 7,285,570.

8. Flavonoids

The compositions of the present invention can comprise a flavonoid compound. Flavonoids are broadly disclosed in U.S. Pat. Nos. 5,686,082 and 5,686,367. Examples of flavonoids particularly suitable for use in the present invention are one or more flavones, one or more isoflavones, one or more coumarins, one or more chromones, one or more dicoumarols, one or more chromanones, one or more chromanols, isomers (e.g., cis/trans isomers) thereof, and mixtures thereof.

Exemplary flavonoids include flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy) and other plant sources of such mixtures (e.g., red clover), and mixtures thereof. Other exemplary materials include flavanones such as hesperitin, hesperidin, and mixtures thereof. Flavonoid compounds useful herein are commercially available from a number of sources, e.g., Indofine Chemical Company, Inc., Steraloids, Inc., and Aldrich Chemical Company, Inc.

In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more flavonoid compounds.

9. N-acyl Amino Acid Compounds

The topical compositions of the present invention can comprise one or more N-acyl amino acid compounds. The amino acid can be one of any of the amino acids known in the art. The N-acyl amino acid compounds of the present invention can correspond to the formula:

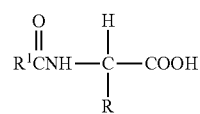

wherein R can be a hydrogen, alkyl (substituted or unsubstituted, branched or straight chain), or a combination of alkyl and aromatic groups. A list of possible side chains of amino acids known in the art are described in Stryer, Biochemistry, 1981, published by W.H. Freeman and Company. $R^1$ can be $C_1$ to $C_{30}$, saturated or unsaturated, straight or branched, substituted or unsubstituted alkyls; substituted or unsubstituted aromatic groups; or mixtures thereof.

The N-acyl amino acid compound may be selected from the group consisting of N-acyl Phenylalanine, N-acyl Tyrosine, their isomers, their salts, and derivatives thereof. The amino acid can be the D or L isomer or a mixture thereof. N-acyl Phenylalanine corresponds to the following formula:

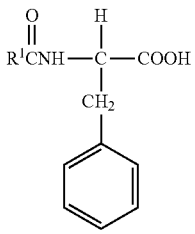

wherein $R^1$ can be $C_1$ to $C_{30}$, saturated or unsaturated, straight or branched, substituted or unsubstituted alkyls; substituted or unsubstituted aromatic groups; or mixtures thereof.

N-acyl Tyrosine corresponds to the following formula:

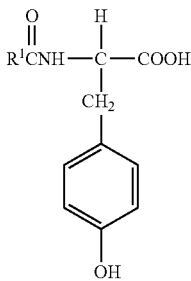

wherein $R^1$ can be $C_1$ to $C_{30}$, saturated or unsaturated, straight or branched, substituted or unsubstituted alkyls; substituted or unsubstituted aromatic groups; or mixtures thereof.

Particularly useful as a topical skin tone evening cosmetic agent is N-undecylenoyl-L-phenylalanine. This agent belongs to the broad class of N-acyl Phenylalanine derivatives, with its acyl group being a C11 mono-unsaturated fatty acid moiety and the amino acid being the L-isomer of phenylalanine. N-undecylenoyl-L-phenylalanine corresponds to the following formula:

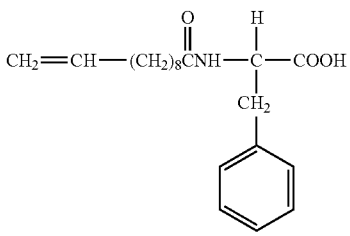

As used herein, N-undecylenoyl-L-phenylalanine is commercially available under the tradename Sepiwhite® from SEPPIC.

In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more N-acyl amino acids.

10. Retinoids

The personal care compositions may comprise one or more retinoid. In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more retinoids. The optimum concentration used in a composition will depend on the specific retinoid selected since their potency can vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid may be selected from retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), or mixtures thereof. Suitable retinoids which are described in U.S. Pat. Nos. 4,677,120; 4,885,311; 5,049,584; 5,124,356; and Reissue 34,075. Other suitable retinoids may include tocopheryl-retinoate [tocopherol ester of retinoic acid (trans- or cis-), adapalene (6-[3-(1-adamantyl)-4-methoxyphenyl]-2-naphthoic acid}, and tazarotene (ethyl 6-[2-(4,4-dimethylthiochroman-6-yl)-ethynyl]nicotinate). Suitable retinoids include retinol, retinyl palmitate, retinyl acetate, retinyl propionate, retinal and combinations thereof. In selected embodiment, retinyl propionate may be used in amounts from about 0.1% to about 0.3%.

11. Peptides

The personal care composition may comprise a peptide. Suitable peptides can include, but are not limited to, di-, tri-, tetra-, penta-, and hexa-peptides and derivatives thereof. In one embodiment, the compositions comprise from about $1\times10^{-7}\%$ to about 20%, from about $1\times10^{-6}\%$ to about 10%, or from about $1\times10^5\%$ to about 5%, by weight of a peptide. In one embodiment, the composition may comprise from about 0.0001%, 0.001%, 0.01%, 0.05%, 0.1%, 0.5%, or 1% to about 25%, 20%, 10%, 7%, 5%, 3%, by weight of the composition, of one or more peptides.

As used herein, "peptide" refers to peptides containing ten or fewer amino acids and their derivatives, isomers, and complexes with other species such as metal ions (e.g., copper, zinc, manganese, magnesium, and the like). Peptide refers to both naturally occurring and synthesized peptides. Also useful herein are naturally occurring and commercially available compositions that contain peptides. The peptides may contain at least one basic amino acid (e.g., histidine, lysine, arginine). For example, suitable peptides are the dipeptide carnosine (beta-ala-his), the tripeptide gly-his-lys, the tripeptide his-gly-gly, the tripeptide gly-gly-his, the tripeptide gly-his-gly, the tetrapeptide gly-gln-pro-arg, the pentapeptide lys-thr-thr-lys-ser, lipophilic derivatives of peptides, and metal complexes of the aforementioned (e.g., copper complex of the tripeptide his-gly-gly (also known as Iamin)). Other suitable peptides include Peptide CK (arg-lys-arg); Peptide CK+(ac-arg-lys-arg-NH2); and Peptide E, arg-ser-arg-lys. A commercially available tripeptide derivative-containing composition is Biopeptide CL® (from Sederma, France), which contains 100 ppm of palmitoyl-gly-his-lys and is commercially available. A commercially available pentapeptide derivative-containing composition is Matrixyl® (from Sederma, France), which contains 100 ppm of palmitoyl-lys-thr-thr-lys-ser. A suitable peptide is a dipeptide based molecule having a C terminal amino acid of threonine, such as plamitoyl-lys-thr, as described in US Patent Application Publication 2007/0020220 A1.

Peptide derivatives useful herein include lipophilic derivatives such as palmitoyl derivatives. In one embodiment, the peptide is selected from palmitoyl-lys-thr-thr-lys-ser, palmitoyl-gly-his-lys, their derivatives, and combinations thereof.

12. Particulate Materials

The compositions of the present invention can comprise one or more additional particulate materials that are not abrasive particles as disclosed herein. Nonlimiting examples of particulate materials useful in the present invention include colored and uncolored pigments, interference pigments, inorganic powders, organic powders, composite powders, optical brightener particles, and combinations thereof. In one embodiment, the composition may comprise from about 0.0001%, 0.001%, 0.01%, 0.05%, 0.1%, 0.5%, 1%, or 2% to about 50%, 25%, 20%, 10%, 7%, 5%, or 3% by weight of the composition, of particulate(s). There are no specific limitations as to the pigment, colorant or filler powders used in the composition.

Particulate materials useful herein can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, polyurethane, aluminum oxide, silicone resin, barium sulfate, calcium carbonate, cellulose acetate, PTFE, polymethyl methacrylate, starch, modified starches such as aluminum starch octenyl succinate, silk, glass, and mixtures thereof. Suitable commercial examples of particulates include, but are not limited to, polymeric particles chosen from the polymethylsilsesquioxane resin microspheres such as including materials sold under the tradename Tospearl® by Momentive Performance Materials Inc., microspheres of polymethylmethacrylates such Micropearl M305 by SEPPIC, spherical particles of crosslinked polydimethylsiloxanes, especially such as those sold by Dow Corning 9506 Cosmetic Power by Dow Corning, spherical particles of polyamide and more specifically Nylon 12 such as Orgasol® 2002 line by Atochem, polystyrene microspheres such as for example those sold under the name Dynospheres® by Dyno Particles, ethylene acrylate copolymer sold under the name EA209 by Kobo, PTFE, polypropylene, aluminum starch ocetenylsuccinate such as those sold under the name Dry-Flo® by AkzoNobel, microspheres of polyethylene such as those sold under the name of Microthene® FN510-00 by Equistar and under then name Micropoly by Presperse, Inc., silicone resin, polymethylsilsesquioxane silicone polymer, and mixtures thereof. Suitable particulate materials include spherical powders with an average primary particle size of from about 0.1 to about 75 microns or from about 0.2 to about 30 microns.

Other suitable particulate materials include interference pigments. Interference pigments, for purposes of the present specification, are defined as thin platelike layered particles having two or more layers of controlled thickness with different refractive indices that yield a characteristic reflected color from the interference of typically two, but occasionally more, light reflections, from different layers of the platelike particle. The most common examples of interference pigments are micas layered with about 50-300 nm films of TiO2, Fe2O3, silica, tin oxide, and/or Cr2O3. Such pigments are often pearlescent. Pearl pigments reflect, refract and transmit light because of the transparency of pigment particles and the large difference in the refractive index of mica platelets and, for example, the titanium dioxide coating. Useful interference pigments are available commercially from a wide variety of suppliers, for example, Rona (Timiron™ and Dichrona™), Presperse (Flonac™), Englehard (Duochrome™), Kobo (KTZ Interfine and KTZ Interval), BASF (Reflecks™) and Eckart (Prestige series). Suitable interference pigments may have a small particle sizes, with an average diameter of individual particles less than about 75 microns in the longest direction, or less than about 50 microns.

Other particulate materials include pigments which can provide color to the personal care composition. Suitable pigments include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or ZrO2, are commercially available from a number of sources. One example of a suitable particulate material contains the material available from U.S. Cosmetics (TRONOX TiO2 series, SAT-T CR837, a rutile TiO2). Suitable pigments include charged dispersions of titanium dioxide, as are disclosed in U.S. Pat. No. 5,997,887.

Colored or uncolored pigments may have a primary average particle size of from about 10 nm, 15 nm, or 20 nm to about 100,000 nm, 5,000 nm, or 1000 nm. Mixtures of the same or different pigments having different particle sizes are also useful herein (e.g., incorporating a TiO$_2$ having a primary particle size of from about 100 nm to about 400 nm with a TiO$_2$ having a primary particle size of from about 10 nm to about 50 nm).

The particulate materials can be surface treated to provide added stability and/or for ease of formulation. Non-limiting examples of suitable coating materials include silicones, lecithin, amino acids, metal soaps, polyethylene and collagen. These surface treatments may be hydrophobic or hydrophilic. Particularly useful hydrophobic pigment treatments include polysiloxane treatments such as those disclosed in U.S. Pat. No. 5,143,722.

13. UV Actives

The compositions of the subject invention may optionally contain a UV active. As used herein, "UV active" includes both sunscreen agents and physical sunblocks. Suitable UV actives may be organic or inorganic. Suitable UV actives are listed in the functional category of "Sunscreen Agents" in the Personal Care Product Council's *International Cosmetic Ingredient Dictionary and Handbook*, Thirteenth Edition, 2010.

Suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone)(commercially available as PARSOL® 1789 from DSM), 2-methyl-5-isopropyl-4'-methoxy dibenzoylmethane, 2-methyl-5-tert-butyl-4'- methoxydibenzoylmethane, 2,4-dimethyl-4'-methoxy dibenzoylmethane, and 2,6-dimethyl-4-tert-butyl-4'-methoxy dibenzoylmethane. Other suitable UV actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethyl-aminophenyl)-5-sulfonicbenzoxazoic acid, octocrylene, zinc oxide, titanium dioxide, and mixtures of these compounds.

Particularly suitable UV actives useful in the compositions of the present invention are 2-ethylhexyl-p-methoxy-cinnamate, 4-tert-butyl-4'-methoxy dibenzoylmethane, 2-hydroxy-4-methoxybenzo-phenone, 2-phenylbenzimidazole-5-sulfonic acid, octocrylene, zinc oxide, titanium dioxide, and mixtures thereof.

Other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), Ethylhexyl triazone (commercially available as Uvinul® T 150 from BASF), Drometrizole trisiloxane (marketed as Mexoryl XL by L'Oreal), Sodium Dihydroxy Dimethoxy Disulfobenzophenone (i.e., benzophenone-9, commercially available as Uvinul® DS 49 from BASF), Diethylamino Hydroxybenzoyl Hexyl Benzoate (commercially available as Uvinul® A Plus from BASF), diethylhexyl butamido triazone (i.e., Iscotrizinol, commercially available as Uvasorb® HEB by 3V Sigma), Polysilicone-15 (i.e., commercially available as PARSOL® SLX from DSM), and Isoamyl p-Methoxycinnamate (i.e., amiloxate, commercially available as Neo Heliopan® E 1000 from Symrise).

14. Photostabilizers

A suitable photostabilizer is alpha-cyanodiphenylacrylate is as disclosed in U.S. Pat. No. 7,713,519. The alpha-cyanodiphenylacrylate may have the general formula:

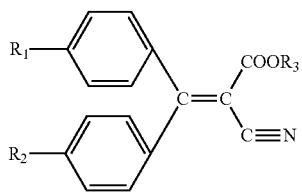

wherein one or both of R1 and R2 is independently a straight or branched chain C1-30 alkoxy radical and any non-alkoxy R1 or R2 radical is hydrogen; and R3 is a straight or branched chain C1-30 alkyl. Alternately, one or both of R1 and R2 is independently a C1-8 alkoxy radical and any non-alkoxy R1 or R2 radical is hydrogen; and R3 is a straight of branched chain C2-20 alkyl. Alternately, one or both of R1 and R2 is independently methoxy, and any non-methoxy R1 or R2 is hydrogen; and R3 is a straight or branched chain C2-20 alkyl.

A suitable alpha-cyanodiphenylacrylate is ethylhexyl methoxycrylene, or 2-ethylhexyl 2-cyano-3-(4-methoxyphenyl)-3-phenylpropenoate, wherein R1 is methoxy, R2 is hydrogen, and R3 is 2-ethylhexyl. This material is available from Hallstar Company under trade name Solastay® S 1.

Another suitable photostabilizer includes diesters or polyesters of naphthalene dicarboxylic acid as disclosed in U.S. Pat. Nos. 5,993,789, 6,113,931, 6,126,925 and 6,284,916. Suitable diesters or polyesters of naphthalene dicarboxylic acid may have the following formula:

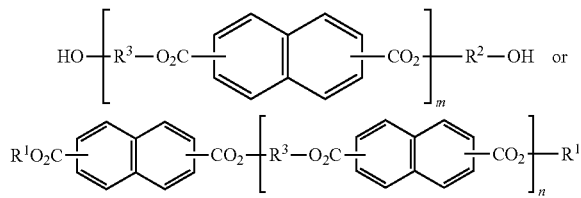

wherein each $R^1$ independently is an alkyl group having 1 to 22 carbon atoms, or a diol having the formula HO—$R^2$—OH, or a polyglycol having the formula HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, 1 to about 10, or 2 to about 7. A suitable diesters of naphthalene dicarboxylic acid is diethylhexyl 2,6-naphthalate available as Corapan® TQ from Symrise.

Another suitable photostabilizer is 4-hydroxybenzylidenemalonate derivatives or 4-hydroxycinnamate derivatives. Suitable materials may have the following formula:

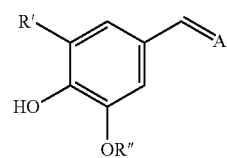

wherein A is a chromophoric group that absorbs UV-radiation, comprises one divalent group or two monovalent groups with at least one group having carbonyl (C=O) functionality; R' is hydrogen, a linear or branched $C_1$-$C_8$ alkyl radical or a linear or branched $C_1$-$C_8$ alkoxy radical; and R" is a linear or branched $C_1$-$C_8$ alkyl radical. Exemplary compounds include ethyl-alpha-cyano-3,5-dimethoxy-4-hydroxy cinnamate, ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, didodecyl-3,5-dimethoxy-4-hydroxy benzylidene malonate, dipalmitoyl-3,5-dimethoxy-4-hydroxy benzylidene malonate, and di-isopropyl-3,5-dimethoxy-4-hydroxy benzylidene malonate. A particularly suitable compound is diethylhexyl syringylidenemalonate (INCI name)

available under the tradename Oxynex® ST from EMD Chemicals, Inc., having the formula:

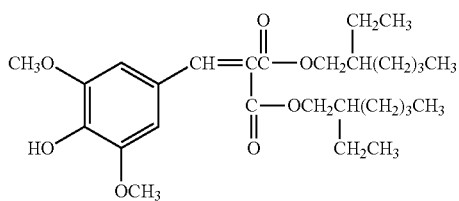

Additional suitable 4-hydroxybenzylidenemalonate derivatives or 4-hydroxycinnamate derivatives are disclosed in U.S. Pat. No. 7,357,919 and U.S. Patent Application Publication No. 2003/0108492A1 and US2003/0157035A.

Another suitable photostabilizer is a 2-pyrrolidinone-4-carboxy ester compounds. Suitable 2-pyrrolidinone-4-carboxy ester compounds may have the following formula:

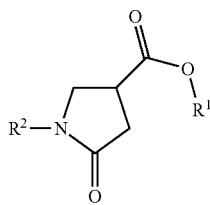

wherein $R^1$ is a linear or branched $C_1$-$C_{20}$ alkyl radical, and $R^2$ is a linear or branched $C_1$-$C_{20}$ alkyl radical which can contain a $C_5$-$C_6$ ring, the phenyl radical, the benzyl radical or the phenethyl radical. Exemplary radicals for $R^1$ and $R^2$ include methyl, ethyl, n-propyl, isopropyl, n-butyl, isobutyl, tert-butyl, n-octyl, 2-ethylhexyl, dodecyl, hexadecyl, cyclohexyl and methylcyclohexyl radicals. Particular examples of 2-pyrrolidinone-4-carboxy ester compounds are provided in U.S. Patent Application Publication No. 2010/0183529.

Other suitable photostabilizers include:
  silicon-containing s-triazines substituted with two aminobenzoate or aminobenzamide groups as described in U.S. Patent Application Publication No. 2008/0145324;
  fluorene derivatives as described in U.S. Patent Application Publications Nos. 2004/00579912, 2004/00579914, 200/00579916, and 2004/062726;
  piperidinol salts as described in U.S. Patent Application Publications No. 2005/0220727 including tris(tetramethylhydroxypiperidinol) citrate sold under the tradename Tinogard® Q by Ciba; and
  arylalkyl amides and esters as described in U.S. Patent Application Publication No. 2008/0019930.

Other suitable photostabilizers are listed in the functional category of "Light Stabilizers" in the Personal Care Product Council's *International Cosmetic Ingredient Dictionary and Handbook*, Thirteenth Edition, 2010.

In one embodiment, the composition may comprise from about 0.0001%, 0.001%, 0.01%, 0.05%, 0.1%, 0.5%, or 1% to about 30%, 25%, 20%, 10%, 7%, or 5%, by weight of the composition, of one or more suitable photostabilizer. In certain embodiments, the personal care composition may comprise at least one photostabilzer and at least one UV active. In particular embodiments, the UV active is a dibenzoylmethane derivative. In a particular embodiment, the UV active is 4,4'-t-butyl methoxydibenzoyl-methane (i.e., avobenzone).

15. Anti-Cellulite Agents

The compositions of the present invention may also comprise an anti-cellulite agent. Suitable agents may include, but are not limited to, xanthine compounds (e.g., caffeine, theophylline, theobromine, aminophylline, chloroethyltheophylline, dyphylline, etamiphylline, proxyphylline, and the like); extracts of tea, coffee, guarana, mate, cola (Cola *nitida*); extracts of climbing ivy (*Hedera helix*), arnica (*Arnica montana* L), rosemary (*Rosmarinus officinalis* N), of marigold (*Calendula officinalis*), sage (*Salvia officinalis* L), ginseng (*Panax ginseng*), St. John's wort (*Hypericum perforatum*), of butcher's broom (Ruscus *aculeatus* L), meadowsweet (*Filipendula ulmaria* L), orthosiphon (*Orthosiphon stamincus* benth), birch (*Betula alba*), cecropia and argan tree; *Ginkgo biloba*, horsetail, escin, cangzhu, *Chrysanthellum indicum, Dioscorea* plants rich in diosgenin or pure diosgenin or hecogenin and compounds thereof, *Ballota, Guioa, Davallia, Terminalia, Barringtonia, Trema, Antirobia*, bitter orange (*Citrus aurantium*); and an extract of cocoa bean shells (*Theobroma cacao*) such as sold under the name Caobromine® by Solabia.

In one embodiment, the personal care composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more anti-cellulite agents.

16. Desquamation Actives

A desquamation active may be added to the compositions of the present invention. In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more desquamation actives.

Suitable desquamation actives include beta-hydroxy acids such as salicylic acid and its derivatives (including 5-(noctanoyl)salicylic acid also known as capryloyl salicylic acid) and alpha-hydroxy acids such as glycolic acid, citric acid, lactic acid, tartaric acid, malic acid or mandelic acid; 8-hexadecene-1,16-dicarboxylic acid or 9-octadecenedioic acid; urea; gentisic acid; oligofucoses; cinnamic acid; *Saphora Japonica* extract; and resveratrol.

Other suitable desquamation actives include compounds acting on the enzymes involved in desquamating or degrading the corneodesmosomes, glycosidases, stratum corneum chymotrypsin enzyme (SCCE) or other proteases (trypsin, chymotrypsin-like). Suitable materials include aminosulphonic compounds such as 4-(2-hydroxyethyl)piperazine-1-propanesulphonic acid (HEPES); 2-oxothiazolidine-4-carboxylic acid (procysteine) and its compounds; compounds of glycine-type alpha-amino acids (as described in U.S. Patent Application Publication No. 2002/0041889, and also sodium methylglycinediacetate sold under the trade name TRILON® M by BASF); honey; and sugar compounds such as O-octanoyl-6-D-maltose and N-acetylglucosamine.

One desquamation system comprises salicylic acid and zwitterionic surfactants as described in U.S. Pat. No. 5,652,228. Another desquamation system contains sulfhydryl compounds and zwitterionic surfactants as described in U.S. Pat. No. 5,681,852

17. Anti-Acne Actives

The compositions of the present invention can comprise one or more anti-acne actives. Suitable anti-acne actives include, but are not limited to, resorcinol, sulfur, salicylic acid, retinoids such as retinoic acid and its derivatives, sulfur-containing amino acids and their derivatives and salts (e.g., N-acetyl derivatives such as N-acetyl-L-cysteine), and lipoic acid. Other suitable anti-acne actives may be chosen from (i) antibiotics and antimicrobials such as benzoyl peroxide, octopirox, tetracycline, 2,4,4' trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; (ii) sebostats such as flavonoids; and (iii) bile salts such as scymnol sulfate and its derivatives, deoxycholate, and cholate. Further examples of suitable anti-acne actives are described in U.S. Pat. No. 5,607,980.

In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more anti-acne compounds.

18. Anti-Oxidants/Racial Scavengers

The compositions of the present invention can include an anti-oxidant/radical scavenger. In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more anti-oxidant/radical scavengers.

Suitable anti-oxidants are listed in the functional category of "Antioxidants" in the Personal Care Product Council's *International Cosmetic Ingredient Dictionary and Handbook*, Thirteenth Edition, 2010.

Suitable anti-oxidants include butylated hydroxytoluene (BHT) and butylated hydroxyanisole (BHA). BHT can be described by the general formula:

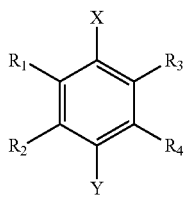

wherein X is OH or SH;
Y is selected from the group consisting of H, OH, $OR_5$, $COOR_5$, alkyl, cycloalkyl, heteroalkyl, heterocycloalkyl, aromatic, heteroaromatic, carboxamido, sulfonamido, carbamate, urea, and trialkylsilyl;
$R_1$, $R_2$, $R_3$, $R_4$ are selected from the group consisting of alkyl, cycloalkyl, heteroalkyl, heterocycloalkyl, aromatic, heteroaromatic, $OR_5$, carboxamido, sulfonamido, formyl, acyl, carboxyl, carboxylate, carbamate, urea, trialkylsilyl, hydroxyl, and hydrogen;
$R_5$ is selected from the group consisting of alkyl, cycloalkyl, heteroalkyl, heterocycloalkyl, aromatic, heteroaromatic, trialkylsilyl, acyl, and hydrogen.

Other anti-oxidants/radical scavengers such as ascorbic acid (vitamin C), tocopherol (vitamin E), tocopherol sorbate, tocopherol acetate, other esters of tocopherol, 6-hydroxy-2, 5,7,8-tetramethylchroman-2-carboxylic acid (commercially available under the tradename Trolox®), amines (e.g., N,N-diethylhydroxylamine, amino-guanidine), nordihydroguaiaretic acid, bioflavonoids, amino acids, silymarin, sorbic acids and its salts, lipoic acid, olive extracts, green tea extracts, white tea extracts, black tea extracts, polyphenols such as proanthocyanidine from pine bark, carotenoids, curcumin compounds such as tetrahydrocurcumin, OCTA (L-2-oxo-4-thiazolidine carboxylic acid), glutathione, and grape skin/seed extracts may be used. Suitable anti-oxidants/ radical scavengers can be selected from esters of tocopherol such as tocopherol acetate.

In one embodiment, the composition comprises tocopherol sorbate. As used herein, "tocopherol sorbate" refers to the sorbic acid ester of tocopherol, a detailed description of which can be found in issued U.S. Pat. No. 5,922,758. In one embodiment, the composition may comprise from about 0.0001%, 0.001%, 0.01%, 0.05%, 0.1%, 0.5%, or 1% to about 50%, 25%, 20%, 10%, 7%, or 5%, by weight of the composition, of the tocopherol sorbate.

19. Conditioning Agents

The personal care compositions of the present invention can contain a safe and effective amount of a conditioning agent selected from, for example, humectants, moisturizers, occlusives, and emollients which may be applied to keratinous tissue. In one embodiment, the composition may comprise from about 0.0001%, 0.001%, 0.01%, 0.05%, 0.1%, 0.5%, or 1% to about 50%, 25%, 20%, 10%, 7%, or 5%, by weight of the composition, of one or more conditioning agents.

Humectants are one group of conditioning agents. Humectants can be selected from the group consisting of polyhydric alcohols, water soluble alkoxylated nonionic polymers, and mixtures thereof. Polyhydric alcohols useful herein include glycerin, sorbitol, propylene glycol, butylene glycol, pentylene glycol, hexylene glycol, ethoxylated glucose, 1, 2-hexane diol, hexanetriol, dipropylene glycol, erythritol, trehalose, diglycerin, xylitol, maltitol, maltose, glucose, fructose, sodium chondroitin sulfate, sodium hyaluronate, hyaluronic acid, sodium adenosine phosphate, sodium lactate, pyrrolidone carbonate, glucosamine, cyclodextrin, and mixtures thereof.

Other conditioning agents include water soluble alkoxylated nonionic polymers such as polyethylene glycols and polypropylene glycols having a molecular weight of up to about 1000 such as those with CTFA names PEG-200, PEG-400, PEG-600, PEG-1000, and mixtures thereof.

Other conditioning agents include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyethylene glycols, sugars (e.g., melibiose), cellulose, dextrin, starches, sugar and starch derivatives (e.g., alkoxylated glucose, fucose), lactamide monoethanolamine, acetamide monoethanolamine, panthenol, allantoin, amylose, hyaluronic acid, sodiium hyaluronate, betaglucan, glycogen, alguronic acid, galactoarabinan and mixtures thereof.

Other conditioning agents are extracts that contain polysaccharides including the following materials: TriMoist KMF (Mibelle AG Biochemistry), Fucogel® and Glycofilm® (Solabia Group), Aquaxyl™ (Seppic), Pheohydrane P (Barnet Products Corporation), Aesthigel (Barnet Products Corporation), Pentacare HP (Pentapharm), and Hyalurosmooth (Laboratoires Serobiologiques).

Also useful herein are the propoxylated glycerols described in U.S. Pat. No. 4,976,953. Also useful are various $C_1$-$C_{30}$ monoesters and polyesters of sugars and related materials. These esters are derived from a sugar or polyol moiety and one or more carboxylic acid moieties. Other suitable conditioning agents are described in U.S. Pat. Nos. 5,750,122; 5,674,478; 4,529,586; 4,507,280; 4,663,158; 4,197,865; 4,217,914; 4,381,919: and 4,422, 853.

20. Anti-Inflammatory Agents

Steroidal anti-inflammatory agents can include, but are not limited to, corticosteroids such as hydrocortisone. In addition, nonsteroidal anti-inflammatory agents can be useful herein. The varieties of compounds encompassed by this group are well known to those skilled in the art. Specific non-steroidal anti-inflammatory agents that can be useful in the composition of the present invention include, but are not limited to, salicylates, flufenamic acid, etofenamate, aspirin, and mixtures thereof.

Additional anti-inflammatory agents useful herein include allantoin and compounds of the Licorice (the plant genus/species *Glycyrrhiza glabra*) family, including glycyrrhetic acid, glycyrrhizic acid, and derivatives thereof (e.g., salts and esters).

In one embodiment, the composition may comprises from about 0.0001%, 0.001%, 0.01%, 0.05%, 0.1%, 0.5%, or 1% to about 50%, 25%, 20%, 10%, 7%, or 5%, by weight of the composition, of one or more anti-inflammatory agents.

21. Tanning Actives

The compositions of the present invention can comprise a tanning active. In one embodiment, the composition may comprises from about 0.0001%, 0.001%, 0.01%, 0.05%, 0.1%, 0.5%, or 1% to about 50%, 25%, 20%, 10%, 7%, or 5%, by weight of the composition, of a tanning active. A suitable tanning active is dihydroxyacetone.

22. Skin Lightening Agents

The compositions of the present invention can comprise a skin lightening agent. In one embodiment, the composition may comprises from about 0.0001%, 0.001%, 0.01%, 0.05%, 0.1%, 0.5%, or 1% to about 50%, 25%, 20%, 10%, 7%, or 5%, by weight of the composition, of one or more skin lightening agents. Suitable skin lightening agents include those known in the art, including ascorbyl glucoside, kojic acid, hydroquinone arbutin, and tranexamic acid. Other skin lightening materials suitable for use herein can include Acitwhite® (Cognis), Emblica® (Rona), Azeloglicina (Sinerga) and extracts (e.g. mulberry extract). An exemplary skin lightening agent is ascorbyl glucoside. Other skin lightening actives include Phlorogine and Phlorgine BG (*laminaria saccharina* extract), deoxyarbutin, sucrose dilaurate, bakuchiol, pyrenoine, millet, arlatone dioic acid, cinnamic acid, ferulic acid, achromaxyl, methyl nicotinamide, oil soluble licorice extract, folic acid, undecylenic acid, zinc undecylenate, L-tryptophan, thiamine HCl, hexylresorcinol, lipidami red vine, dragosine, methyl gentisate, inositol, 1,2-hexandiol and 1,2-octandiol (available as Symdiol 68 from Symrise), laminaine, their salts, their derivatives, their precursors, and combinations thereof. Suitable skin lightening agents are further disclosed in U.S. Patent Application Publication US 2010/0189669 A1.

23. Botanical Extracts

The personal care composition may comprise botanical extracts. In one embodiment, the composition may comprises from about 0.0001%, 0.0005% 0.001%, 0.01%, 0.05%, 0.1%, 0.5%, or 1% to about 30%, 25%, 20%, 10%, 7%, 5%, 3%, by weight of the composition, of one or more botanical extracts. Suitable botanical extracts include extracts from plants (herbs, roots, flowers, fruits, seeds) such as flowers, fruits, vegetables, and so on, including yeast ferment extract, *Padina Pavonica* extract, *thermus thermophilis* ferment extract, *camelina sativa* seed oil, *boswellia serrata* extract, olive extract, *bodopsis Thaliana* extract, *Acacia Dealbata* extract, *Acer Saccharinum* (sugar maple), acidopholus, acorus, *aesculus*, Alicaligenes polysaccharides, *agaricus*, agave, agrimonia, algae, aloe, citrus, *brassica*, cinnamon, orange, apple, blueberry, cranberry, peach, pear, lemon, lime, pea, seaweed, caffeine, green tea, chamomile, willowbark, mulberry, poppy, and the like. Further specific examples include, but are not limited to, *Glycyrrhiza Glabra, Salix Nigra,* Macrocycstis Pyrifera, *Pyrus Malus,* Saxifraga *Sarmentosa, Vitis Vinifera, Morus Nigra, Scutellaria Baicalensis, Anthemis Nobilis, Salvia Sclarea, Rosmarinus Officianalis, Citrus Medica Limonum, Ginkgo Biloba Panax Ginseng, Siegesbeckia Orientalis, Fructus Mume, Ascophyllum Nodosum, Bifida Ferment* lysate, *Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea, Laminaria Angustata, Laminaria Cloustoni, Laminaria Digitata, Laminaria Digitata, Laminaria Hyperborea, Laminaria Japonica, Laminaria Longissima, Laminaria Ochotensis, Laminaria Ochroleuca, Laminaria Saccharina,* and mixtures thereof. Other suitable actives are listed in the functional category of "Biological Products" in the Personal Care Product Council's *International Cosmetic Ingredient Dictionary and Handbook*, Thirteenth Edition, 2010.

24. Antimicrobial, Antibacterial and Antifungal Actives

The personal care compositions can comprise an antimicrobial or antifungal active. A safe and effective amount of an antimicrobial or antifungal active can be added to the present compositions. In one embodiment, the composition may comprises from about 0.0001%, 0.001%, 0.01%, 0.05%, 0.1%, 0.5%, or 1% to about 30%, 25%, 20%, 10%, 7%, 5%, or 3%, by weight of the composition, of one or more antimicrobial, antibacterial and/or antifungal actives.

Suitable actives useful herein include those selected from the group consisting of benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, phytic acid, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, lidocaine hydrochloride, neocycin sulfate, and mixtures thereof.

Suitable antimicrobial actives include coal tar, sulfur, whitfield's ointment, castellani's paint, aluminum chloride, gentian violet, octopirox (piroctone olamine), 2,4,4'-trichloro-2'-hydroxy diphenyl ether (Triclosan), 3,4,4'-trichlorocarbanilide (Triclocarban), ciclopirox olamine, undecylenic acid and metal salts, potassium permanganate, selenium sulfide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, ethylhexylglycerin, hexamidine diisethionate, azelaic acid, lyticase, iodopropynyl butylcarbamate (IPBC), isothiazalinones such as octyl isothiazalinone, and combinations thereof.

Azole antimicrobials may be used and include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof.

Selenium sulfide may be used as an antimicrobial. Selenium sulfide is generally regarded as a compound having one mole of selenium and two moles of sulfur, although it may also be a cyclic formula that conforms to the general formula Se$_x$S$_y$, wherein x+y=8. Average particle diameters for the selenium sulfide are typically less than 15 μm, as measured by forward laser light scattering device (e.g., Malvern 3600 instrument), or, alternately, less than 10 μm. Selenium sulfide compounds are described, for example, in U.S. Pat. Nos. 2,694,668, 3,152,046, 4,089,945, and 4,885,107.

Other suitable actives are listed in the functional category of "Cosmetic Biocides" in the Personal Care Product Council's *International Cosmetic Ingredient Dictionary and Handbook*, Thirteenth Edition, 2010.

25. Antiperspirant Actives

Antiperspirant actives may also be included in the compositions of the present invention. Suitable antiperspirant actives include astringent metallic salts, especially the inorganic and organic salts of aluminum zirconium and zinc, as well as mixtures thereof. Exemplary actives include aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof. In one embodiment, the composition may comprises from about 0.0001%, 0.001%, 0.01%, 0.05%, 0.1%, 0.5%, or 1% to about 30%, 25%, 20%, 10%, 7%, 5%, or 3% by weight of the composition, of one or more antiperspirant compounds.

26. Sensates

The personal care composition may include a warming sensates and/or cooling senate. Sensates provide the sensation of heating or cooling to a user, but may or may not yield a change in skin temperature. The sensation may be instantaneous or may be delayed, but, generally, is appreciable within 5 minutes of application of the skin care composition. In one embodiment, the composition may comprises from about 0.0001%, 0.001%, 0.01%, 0.05%, 0.1%, 0.5%, or 1% to about 30%, 25%, 20%, 10%, 7%, 5%, or 3%, by weight of the composition, of one or more sensates. Any mixture of the warming and/or cooling sensates may also be used.

Suitable warming sensates include vanillyl alcohol derivatives including of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether and vanillyl alcohol ethyl ether; and phosphate derivatives comprising the aforementioned vanillyl alcohol derivatives such as vanillyl alcohol isoamyl ether monophosphate, vanillyl alcohol n-butyl ether monophosphate, vanillyl alcohol n-hexyl ether monophosphate. Other suitable warming sensates include ethyl alcohol, niacin, jambu, nicotinic acid, zingerone, vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, methyl salicylate, shogaol paradol, zingerone, capsaicin, dihydrocapsaicin, nordihydrocapsaicin, homocapsaicin, homodihydrocapsaicin, ethanol, tincture capsicum, oleoresin ginger alcohol extraction, *eucalyptus* oil, capsaicin, cinnamic aldehyde, chloroform, ether, iso-Amyl alcohol, benzyl alcohol, allyl isothiocyanate, ethyl acetate, glycerine, limonene, menthol, 4-hydroxy-4-methyl-cyclohexen-2-one-1, and mixtures thereof. Further suitable warming sensates include fluid extracts, hydro-alcohol extracts, essential oils, oleoresins, concretes or distillates of mustard seed, ginger, horseradish, chillies, jalapeno, pepper, capsicum, clove, cassia, and mixtures thereof.

Suitable cooling sensates include menthol, isopulegole, 3-(1-menthoxy)propan-1,2-diol, p-menthan-3,8-diol, 6-isopropyl-9-methyl-1,4-dioxaspiro-(4,5)-decane-2-methanol, menthyl succinate, alkaline earth salts of menthyl succinate, trimethyl cyclohexanol, N-ethyl-2-isopropyl-5-methylcyclohexane carboxamide and other carboxamides as described in U.S. Pat. Nos. 4,136,163 and 4,230,688, 3-(1-menthoxy)-2-methyl-propan-1,2-diol, mint oil, peppermint oil, wintergreen, menthone, menthone glycerin ketal and other glycerol ketals described in U.S. Pat. No. 5,266,592, menthyl lactate, 2-(5'-methyl-2-(methylethyl)cyclohexyloxy)ethan-1-ol, 3-(5'-methyl-2'-(methylethyl)cyclohexyloxy)propan-1-ol, 4-(5'-methyl-2'-(methylethyl) cyclohexyloxy) butan-1-ol, and spearmint. Other cooling sensates include p-menth-3-yl n-butyl sulphoxide, n-butyl 1-isobutylcyclohexyl sulphoxide, n-hexyl 1-isobutylcyclohexyl sulphoxide, n-butyl 1-isoamylcyclohexyl sulphoxide and n-hexyl 1,2-diethylcyclohexyl sulphoxide, and other cyclic sulphoxides and sulphones as described in U.S. Pat. No. 4,032,661.

27. Preservatives

In one embodiment, the composition may comprises from about 0.0001%, 0.001%, 0.01%, 0.05%, 0.1%, 0.5%, or 1% to about 10%, 7%, 5%, 2%, or 1%, by weight of the composition, of one or more preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, sodium benzoate, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM hydantoin, DEDM hydantoin dilaurate, dehydroacetic acid, diazolidinyl urea, dibromopropamidine diisethionate, DMDM hydantoin, glyceryl caprylate, potassium sorbate, salicylic acid, hexamidine, capryloyl glycine, 1,2 hexanediol, undecylenoyl glycine, ethylhexylglycerin, caprylhydroxamic acid, methylpropanediol, hinokitiol, sodium hinokitiol, phenylethyl alcohol, levulinec acid, p-anisic acid, 2-bromo-2-nitropropane-1,3-diol, sodium hydroxymethylglycinate, iodopropynyl butylcarbamate, methylchloroisothiazolinone, methylisothiazolinone, piroctone olamine, cinnamon oil, rosemary extract, Biopein® (available form Bio-Botanica), Naticide® (available form Sinerga), and combinations thereof. In one embodiment, the composition is free of parabens and/or formaldehydes.

28. Anti-dandruff Actives

The personal care compositions of the present invention may also contain an anti-dandruff agent. In one embodiment, the personal care composition may comprises from about 0.0001%, 0.001%, 0.01%, 0.05%, 0.1%, 0.5%, or 1% to about 20%, 10%, 7%, 5%, 4%, 3%, or 2%, by weight of the composition, of one or more anti-dandruff actives. Suitable, non-limiting examples of anti-dandruff particulates include: pyridinethione salts, azoles, selenium sulfide, particulate sulfur, and mixtures thereof. In a particular embodiment, pyridinethione anti-dandruff particulates, especially 1-hydroxy-2-pyridinethione salts, may be used. Suitable pyridinethione salts include those formed from heavy metals such as zinc, tin, cadmium, magnesium, aluminum and zirconium. In particular, zinc or a zinc salt of 1-hydroxy-2-pyridinethione (known as "zinc pyridinethione" or "ZPT") may be used. 1-hydroxy-2-pyridinethione salts may be in platelet particle form, wherein the particles have an average size of up to about 20μ, up to about 5, or up to about 2.5. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

29. Substantivity Polymers

The personal care composition can comprise one or more substantivity polymers. These polymers may be used to enhance the deposition and longevity of other ingredients onto the keratinous tissue. These polymers may also improve rub-off resistance and water repellence. In one embodiment, the composition may comprises from about 0.0001%, 0.001%, 0.01%, 0.05%, 0.1%, 0.5%, or 1% to about 30%, 25%, 20%, 10%, 7%, 5%, or 3%, by weight of the composition, of one or more substantivity polymer.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (INCI name: Polyquaternium-16); copolymers of 1-vinyl-2-pyrrolidone and dimethylaminoethyl methacrylate (INCI name: Polyquaternium-11); cationic diallyl quaternary ammonium-containing polymers, including, for example, dimethyldiallylammonium chloride homopolymer, copolymers of acrylamide and dimethyldiallylammonium chloride (INCI name: Polyquaternium 6 and Polyquaternium 7, respectively); amphoteric copolymers of acrylic acid including copolymers of acrylic acid and dimethyldiallylammonium chloride (INCI name: Polyquaternium 22), terpolymers of acrylic acid with dimethyldiallylammonium chloride and acrylamide (INCI name: Polyquaternium 39), and terpolymers of acrylic acid with methacrylamidopropyl trimethylammonium chloride and methylacrylate (INCI name: Polyquaternium 47). Preferred cationic substituted monomers are the cationic substituted dialkylaminoalkyl acrylamides, dialkylaminoalkyl methacrylamides, and combinations thereof. These preferred monomers conform to the formula:

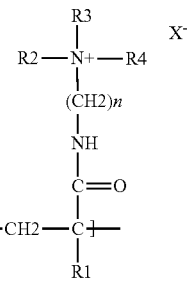

wherein $R^1$ is hydrogen, methyl or ethyl; each of $R^2$, $R^3$ and $R^4$ are independently hydrogen or a short chain alkyl having from about 1 to about 8 carbon atoms; n is an integer having a value of from about 1 to about 8; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc.

Other suitable cationic polymers for use in the composition include polysaccharide polymers, such as cationic cellulose derivatives and cationic starch derivatives. Suitable cationic polysaccharide polymers include those which conform to the formula:

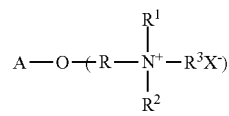

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms; and X is an anionic counterion as described in hereinbefore.

Suitable cationic cellulose polymers are salts of hydroxyethyl cellulose reacted with trimethyl ammonium substituted epoxide, INCI name "Polyquaternium 10" and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide, INCI name "Polyquaternium 24." These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially avaialable from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581.

The compositions herein can comprise nonionic polymers. For instance, polyalkylene glycols having a molecular weight of more than about 1000 can be used. These can include those having the following general formula:

$$H(OCH_2CRH)_n-OH$$

wherein R is selected from the group consisting of H, methyl, and mixtures thereof; and n is a value selected such that the molecular weight of the molecule is greater than 1000 Da. Preferred polyethylene glycol polymers can include PEG-2M (also known as Polyox WSR® N-10, which is available from Dow Chemical Co. and as PEG-2, 000); PEG-5M (also known as Polyox WSR® N-35 and Polyox WSR® N-80, available from Dow and as PEG-5,000 and Polyethylene Glycol 300,000); PEG-7M (also known as Polyox WSR® N-750 available from Dow); PEG-9M (also known as Polyox WSR® N-3333 available from Dow); and PEG-14 M (also known as Polyox WSR® N-3000 available from Dow).

Suitable commercially available substantivity polymers include: Cosmedia DC (hydrogenated dimer Dilinoleyl/Dimethylcarbonate Copolymer) available from Cognis; Polycrylene (copolymer of adipic acid and neopentyl glycol end-capped with either octyldodecanol or a cyanodiphenyl-propenoyl group). Polycrylene has the INCI name Polyester-8 and is available from Hallstar Co; Dow Corning FA 4001 CM Silicone Acrylate and Dow Corning FA 4002 ID Silicone Acrylate (copolymer of polytrimethylsiloxymethacrylate and one or more monomers consisting of acrylic acid, methacrylic acid, or one of their simple esters dissolved in cyclopentasiloxane or isododecane, respectively); Ganex P-904 (poly(butylated vinylpyrrolidone)), Ganex V-216 (vinylpyrrolidone and hexadecene copolymer), Ganex V-220 (vinylpyrrolidone and eicosene copolymer), and Ganex WP-660 (vinyl pyrrolidone and 1-triacontane copolymer), all available from International Specialty Products; Phospholipon 90H (hydrogenated lecithin) available from Phospholipid GmbH; Dermacryl AQF (acrylates copolymer) available from National Starch and Chemical Company; Stantiv OMA-2 (octadecene and maleic anhydride copolymer) available from Vertellus Performance Materials, Inc.; Dermacryl-79 (copolymer of octylacrylamide and one or more monomers consisting of acrylic acid, methacrylic acid or one of their simple esters) available from National Starch and Chemical Company; Allianz OPT (copolymer of: methacrylic acid, methyl methacrylate, butyl acrylate, and cetyl-eicosinyl methacrylate) available from International Specialty Products; and Avalure UR 450 (PPG-17, isophorone diisocyanate and dimethylol propionic acid copolymer) available from Noveon.

Other suitable polymers are disclosed in paragraph 50 of U.S. Patent Application Publication No. 2006/0134045 A1.

30. Detersive Surfactants

Depending upon the form and function, the personal care composition may include one or more detersive surfactants. In certain embodiments, the personal care composition may be in the form of a leave-on product that may be substantially free of cleansing or detersive surfactants. For example, leave-on compositions may comprise less than 1% cleansing surfactants, less than 0.5% cleansing surfactants, or 0% cleansing surfactants If and when present, the detersive surfactant component can be included to provide cleaning performance to the composition. The detersive surfactant component in turn can comprise anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. When included, the concentration of the anionic surfactant component in the composition can preferably be sufficient to provide the desired cleaning and lather performance, which generally can range from about 1%, 2.5%, 5%, 7.5%, 10%, 12.5%, or 15% to about 50%, 40%, 30%, 25%, 20%, or 10%, by weight of the composition.

Suitable anionic surfactants suitable for use in the compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

In certain embodiments, R has from about 8 to about 18 carbon atoms, from about 10 to about 16 carbon atoms, or from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, from about 2 to about 5, or about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1—SO_3-M]$ where $R^1$ is a straight or branched chain, saturated, aliphatic hydrocarbon radical having from about 8 to about 24 or from about 10 to about 18 carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921, 2,486, 922, and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the personal care composition is beta-alkyloxy alkane sulfonates. These surfactants conform to the formula

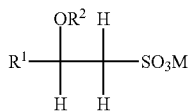

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Suitable anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof. Non limiting examples of suitable zwitterionic or amphoteric surfactants are described in U.S. Pat. Nos. 5,104,646 and 5,106,609.

Zwitterionic detersive surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. Non limiting examples of other anionic, zwitterionic, amphoteric or optional additional surfactants suitable for use in the compositions are described in McCutcheon's, *Emulsifiers and Detergents,* 2010 Annual Ed., published by M. C. Publishing Co., and U.S. Pat. Nos. 3,929,678, 2,658,072, 2,438,091, and 2,528,378.

Any other suitable optional component can also be included in the personal care composition of the present invention, such as those ingredients that are conventionally used in given product types. The Personal Care Product Council's *International Cosmetic Ingredient Dictionary and Handbook*, Thirteenth Edition, 2010, describes a wide variety of nonlimiting functional materials that can be added to the composition herein. Examples of these functional classes include, but are not limited to: abrasives, absorbents, fragrances, anti-acne agents, anti-caking agents, antifoaming agents, antimicrobial agents (e.g., iodopropyl butylcarbamate), antifungal agents, antioxidants, binders, buffering agents, bulking agents, chelating agents, colorants, cosmetic astringents, cosmetic biocides, denaturants, drug astringents, external analgesics, film formers, opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching agents, skin-conditioning agents (e.g. humectants and occlusive agents), and skin protectants. Other suitable optional person care ingredients include materials listed in paragraphs 513-839 of U.S Patent Application No. 2010/0112100.

Improved Efficacy Test

The efficacy of a personal care composition comprising abrasive particles can be compared to a personal care composition contained conventional particles and no particles. The examples are provided below:

| (values in wt %) | Ex. 1 | Ex. 2 | Ex. 3 | Ex. 4 |
|---|---|---|---|---|
| Water | QS | QS | QS | QS |
| Sodium Cocoyl Isethionate | 18.000 | 18.000 | 18.000 | 18.000 |
| Glycerin | 18.000 | 18.000 | 18.000 | 18.000 |
| Lauramidopropyl Betaine | 8.571 | 8.571 | 8.571 | 8.571 |
| Acrylates Copolymer | 4.167 | 4.167 | 4.167 | 4.167 |
| PEG-7M | 0.100 | 0.100 | 0.100 | 0.100 |
| Disodium EDTA | 0.100 | 0.100 | 0.100 | 0.100 |
| Perfume | 0.300 | 0.300 | 0.300 | 0.300 |

-continued

| (values in wt %) | Ex. 1 | Ex. 2 | Ex. 3 | Ex. 4 |
|---|---|---|---|---|
| Menthol | 0.100 | 0.100 | 0.100 | 0.100 |
| Methylchloroisothiazolinone & Methylisothiazolinone | 0.030 | 0.030 | 0.030 | 0.030 |
| Abrasive Particle A *1 | — | — | 3.000 | — |
| Abrasive Particle B *2 | — | — | — | 3.000 |
| Oxidized polyethylene *3 | — | 3.000 | — | — |

*1 A foamed and reduced cross-linked styrene-co-divinyl benzene copolymer with approximately a 50:50 weight ratio of styrene to DVB 55 (DVB 55 a mixture of divinyl benzene and ethyl vinyl benzene in the weight ratio of 55:45, commercially available from the Dow Chemical Co.) with the following particle parameters: mean ECD = 118 microns, mean Roughness = 0.11, mean Circularity = 0.40; and mean Solidity = 0.80.
*2 A foamed and reduced cross-linked styrene-co-divinyl benzene copolymer with approximately a 50:50 weight ratio of styrene to DVB 55 (DVB 55 a mixture of divinyl benzene and ethyl vinyl benzene in the weight ratio of 55:45, commercially available from the Dow Chemical Co.) with the following particle parameters: mean ECD = 218 microns, mean Roughness = 0.11, mean Circularity = 0.40; and mean Solidity = 0.82.
*3 Asensa ®SC 240 available from Allied Signal Inc., Morristown, NJ. Supplier reported average particle size of 125 micrometers.

Figure 4:
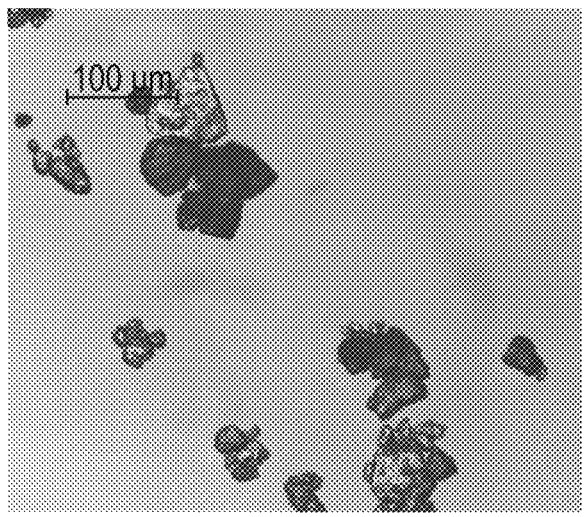
FIG. 4 is an electron microscopy image showing oxidized polyethylene particles.

FIG. 4 is an electron microscopy image showing oxidized polyethylene particles from Example 2.

Figure 5:
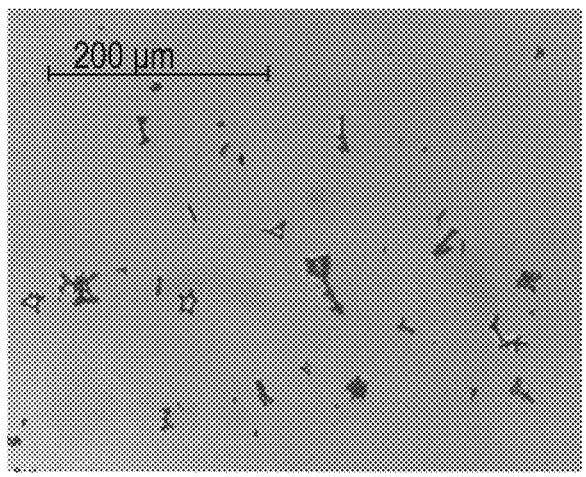
FIG. 5 is an electron microscopy image showing abrasive particles A.
Figure 6:
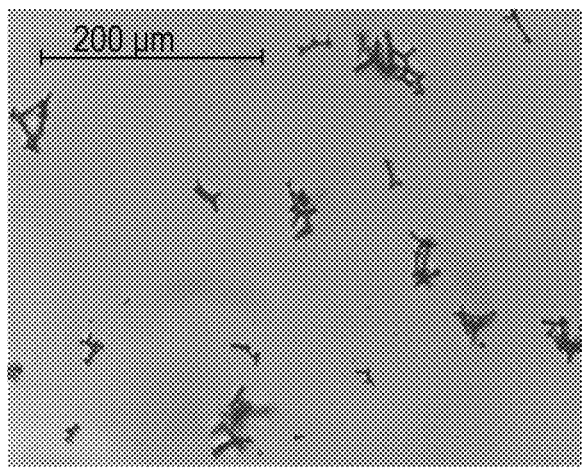
FIG. 6 is an electron microscopy image showing abrasive particles B.

FIG. 5 is an electron microscopy image showing the abrasive particle A from Example 3. FIG. 6 is an electron microscopy image showing the abrasive particle B from Example 4.

The cleansing efficacy of Examples 1-4 may be tested according to the following method. The volar forearm of a test subject is marked into four 4 cm×3 cm sites. Makeup (i.e., Elizabeth Arden Flawless Finish Sponge-on Cream Makeup—warm beige) is applied to each of the four sites. For each site, apply the makeup by dosing a makeup sponge by swiping the sponge across the makeup three times with moderate pressure. Swipe the loaded sponge across a test site three times (with moderate pressure) keeping makeup inside of site. Allow the makeup to dry for 5 minutes. Cleanse one site with an exemplary formulation. Approximately 0.50 cm³ of the exemplary cleanser product is applied to the test site. Rub the cleanser within the site using the index and middle fingers together in a circular/up and down motion for 15 seconds. Rinse the site under running water while rubbing with the index and middle fingers together in a circular motion/up and down motion for 10 seconds. Gently pat the site dry with paper towels taking care not to remove any makeup residue. Allow the site to dry for 5 minutes. The makeup residue on the test site is removed by using a clean cotton round (e.g., Johnson's Pure Cotton Cosmentic Rounds from Johnson & Johnson) dosed with 1000 ul of a make-up remover (e.g., Lancome Bi-Facil makeup remover). Swipe the test site with the dosed pad twice by wrapping pad around middle finger holding firmly in place with the index and third finger. Turn pad 180° and swipe the test site twice in a direction perpendicular to the first two swipes. Color values of the residual makeup collected on the cotton round is analyzed using a chromameter (e.g., Minolta Chromameter CR-200). Measurements are taken at the center of the cotton round where the residual makeup was collected. Obtained three measurements of color values of L*, a*, and b* for each cotton round. Calculate an average delta E (i.e., total color difference). The delta E for Examples 1-4 are reported in the table below. Sensory feel data is subjective evaluation of the texture of the examples.

| Example | Sensory Feel | Delta E |
|---|---|---|
| Ex. 1 | Smooth | 33.264 |
| Ex. 2 | Scrubby, hard, a bit of harsh | 30.669 |
| Ex. 3 | A bit of Scrubby, not hard | 23.935 |
| Ex. 4 | Smooth | 23.314 |

A High Delta E value indicates more residue left on the skin by the product and a low Delta E value indicates low makeup residue. The test results demonstrate that the personal care compositions with the abrasive particles described herein provide better cleaning efficacy while providing an acceptable feel profile.

Exemplary Personal Care Composition

The following formulations are non-limiting prophetic examples of suitable personal care compositions. Where applicable, ingredients are referenced by INCI name. While particular embodiments of the subject invention have been described, it will be obvious to those skilled in the art that various changes and modifications to the subject invention can be made without departing from the spirit and scope of the invention. Examples 1-12 are skin care compositions that have the benefit of improved exfoliation and/or microdermabrasion as provided by the abrasive particles.

| | Examples (values are weight %) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| PHASE A | | | | | | | | | | | | |
| DC-9040 *1 | 5.10 | 13.5 | | | q.s to 100 | | | | | | | |
| DC-9045 *2 | | | 15 | 15 | | | 32.75 | 14.0 | | 14.0 | | |
| PEG-4 | | | | | | | | | | | | q.s to 100 |
| Dimethicone | 4.10 | | 6 | 6 | | | | 5.2 | | 5.2 | | |
| Polymethylsilsesquioxane *3 | 4.10 | 7.5 | | | | | | | 0.5 | | | 0.5 |
| Polyethylene beads *4 | | | | | | | | | | 2.0 | 2.0 | |
| Cyclomethicone | 11.4 | 23.5 | 15 | 15 | | q.s to 100 | 10.0 | 1.05 | | 1.05 | | |
| KSG-210 *5 | 5.40 | 2.5 | | | | | | | | | | |
| KSG-310 *6 | | | | | | 20.0 | | | | | | |
| Polyethylene wax *7 | 2.05 | | | | | | | | | | | |
| DC-2503 Cosmetic Wax *8 | 3.77 | | | | | | 1.5 | | | | | |
| Abil EM97 *9 | | 0.45 | | | | | | | 0.45 | | | |

-continued

|  | Examples (values are weight %) | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| KF 6017 *10 |  | 0.375 |  |  |  |  |  |  |  |  |  |  |
| Cetyl Ricinoleate |  | 0.25 |  |  |  |  |  |  |  |  |  |  |
| KTZ Fine TiO$_2$ coated Mica *11 | 1.00 |  |  |  |  |  |  |  |  |  |  |  |
| Dow Corning 1503 *12 |  |  | 3 | 3 |  |  |  | 3.5 |  | 3.5 |  |  |
| Octisalate |  |  |  |  | 4.0 | 4.0 |  |  |  |  |  |  |
| Homosalate |  |  |  |  | 4.0 | 4.0 |  |  |  |  |  |  |
| Octocrylene |  |  |  |  | 1.5 | 1.5 |  |  |  |  |  |  |
| Avobenzene |  |  |  |  | 2.0 | 2.0 |  |  |  |  |  |  |
| Isopropyl Lauroylsarcosinate |  |  |  |  | 7.5 | 7.5 |  |  |  |  |  |  |
| Tospearl 145A *13 |  |  |  |  | 10 | 10 |  |  |  |  |  |  |
| Prestige Fire Red 11S2 *14 |  |  |  |  | 0.1 | 0.1 |  |  |  |  |  |  |
| Microthene FN-510 *15 |  |  | 9 | 9 |  |  |  | 10.0 |  | 10.0 |  |  |
| Petrolatum |  |  |  |  |  |  | 0.5 |  |  |  |  |  |
| Isohexadecane |  |  |  |  |  |  |  |  | 3.0 |  |  | 3.0 |
| Isopropyl Isostearate |  |  |  |  |  |  |  |  | 1.0 |  |  | 1.0 |
| Stearic Acid |  |  |  |  |  |  |  |  | 0.4 |  |  | 0.4 |
| Cetearyl Glucoside |  |  |  |  |  |  |  |  | 0.2 |  | 0.5 | 0.2 |
| Cetyl Alcohol |  |  |  |  |  |  |  |  | 1.0 |  | 1.3 | 1.0 |
| Stearyl Alcohol |  |  |  |  |  |  |  |  |  |  | 20.0 |  |
| Magnesium Sulfate Anhydrous |  |  |  |  |  |  |  |  |  |  | 3.0 |  |
| PEG/PEG-300/55 Copolymer |  |  |  |  |  |  |  |  |  |  | 2.0 |  |
| Tego Care CP *16 |  |  |  |  |  |  |  |  |  |  | 1.78 |  |
| Econol TM-22 *17 |  |  |  |  |  |  |  |  |  |  | 0.80 |  |
| Distearyldimonium chloride |  |  |  |  |  |  |  |  |  |  | 0.25 |  |
| Hydroxypropylcellulose Petrolatum |  |  |  |  |  |  | 0.5 |  |  |  | 0.15 |  |
| Fragrance | 0.10 |  |  |  | 0.2 | 0.2 |  |  |  |  |  |  |
| PHASE B | | | | | | | | | | | | |
| Glycerin | 10.0 | 10.0 | 11 | 11 |  |  | 10 | 10.0 | 2.0 | 10.0 |  | 2.0 |
| Panthenol | 0.5 | 1.00 | 0.7 | 0.7 |  |  | 1.0 | 1.0 |  | 1.0 |  |  |
| Pentylene Glycol | 3.00 |  |  |  |  |  |  |  |  |  |  |  |
| Propylene Glycol |  | 1.00 |  |  |  |  | 1.0 | 1.0 |  | 1.0 |  |  |
| Butylene Glycol |  | 1.00 |  |  |  |  | 1.0 | 1.0 |  | 1.0 |  |  |
| Tocopherol Acetate |  | 0.50 | 0.2 | 0.2 |  |  | 0.5 | 0.5 | 0.5 | 0.5 |  | 0.5 |
| N-Acetyl Glucosamine | 0.50 |  | 2.0 | 2.0 |  |  |  |  |  |  |  |  |
| Hexamidine Diisethanoate *18 | 0.10 |  |  |  |  |  |  |  |  |  |  |  |
| Niacinamide | 5.00 | 4.00 | 5.00 | 5.00 |  |  | 5 | 5.0 | 2.5 | 5.0 |  | 2.5 |
| Methylparaben | 0.20 | 0.10 |  |  |  |  | 0.1 |  |  |  |  |  |
| Ethylparaben | 0.05 | 0.10 |  |  |  |  | 0.1 | 0.1 |  | 0.1 |  |  |
| Benzyl Alcohol | 0.25 | 0.50 |  |  |  |  | 0.4 | 0.4 |  | 0.4 | 0.1 |  |
| Propyl Paraben |  | 0.10 |  |  |  |  | 0.1 | 0.1 |  | 0.1 |  |  |
| Disodium EDTA |  | 0.10 | 0.05 | 0.05 |  |  | 0.1 |  | 0.1 |  |  | 0.1 |
| Polysorbate 20 |  |  | 0.6 | 0.6 |  |  |  | 0.8 |  | 0.8 |  |  |
| Glydant Plus Liquid *19 |  |  | 0.3 | 0.3 |  |  |  |  |  |  |  |  |
| Laureth-4 |  |  | 0.2 | 0.2 |  |  |  | 0.2 |  | 0.2 |  |  |
| Sucrose Polycottonseedate |  |  |  |  |  |  | 0.5 |  |  |  |  |  |
| Allantoin |  |  |  |  |  |  | 0.1 | 0.2 |  | 0.2 |  |  |
| Prodew 400 *20 |  |  |  |  |  |  |  |  |  |  |  |  |
| GLW75CAP-MP *21 |  |  |  |  |  |  |  | 0.35 |  | 0.35 |  |  |
| Hydrolyzed wheat protein |  |  |  |  |  |  |  |  | 2.0 |  |  |  |
| Menthol |  |  |  |  |  |  |  |  |  |  |  | 0.5 |
| Vanillyl alcohol isoamyl ether monophosphate |  |  |  |  |  |  |  |  |  |  |  | 0.05 |
| Sodium Chloride | 0.50 |  |  |  |  |  |  |  |  |  |  |  |
| FD&C Red No. 40 |  |  |  |  |  |  | .00025 |  |  |  |  |  |
| FD&C Blue 1 |  |  |  |  |  |  | .0001 |  |  |  |  |  |
| Sepigel 305 *22 |  |  | 1.6 |  |  |  |  | 1.5 | 1.5 | 1.5 |  | 1.5 |

-continued

| | Examples (values are weight %) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Water | q.s to 100 | q.s to 100 | q.s to 100 | q.s to 100 | | | q.s to 100 | q.s to 100 | q.s to 100 | q.s to 100 | | q.s to 100 |
| Abrasive Particle A and/or B *23 | | | | | | 0.1%-10% | | | | | | |

*1 12.5% Dimethicone Crosspolymer in Cyclopentasiloxane. Available from Dow Corning.
*2 Dimethicone Crosspolymer in Cyclopentasiloxane. Available from Dow Corning.
*3 E.g.,Tospearl USA or Tospearl 2000. Available from GE Toshiba Silicone
*4 PFM (250-500 μm) colored beads from Kobo.
*5 25% Dimethicone PEG-10/15 Crosspolymer in Dimethicone. Available from Shin-Etsu
*6 PEG-15/Lauryl Dimethicone Crosspolymer in Mineral Oil from Shin-Etsu.
*7 Jeenate 3H polyethylene wax. Available from Jeen
*8 Stearyl Dimethicone. Available from Dow Corning.
*9 Bis-PEG/PPG-14/14 Dimethicone. Available from Degussa
*10 PEG-10 Dimethicone. Available from Shin-Etsu.
*11 Hydrophobically modified $TiO_2$ coated Mica. Available from Kobo.
*12 Dimethicone/Dimethiconol blend from Dow Corning.
*13 Polymethylsilsesquioxane from General Electric.
*14 Mica and iron oxides from Eckart.
*15 Polyethylene powder available from Equistar.
*16 Dioleoylethyl hydroxyethylmonium methosulfate mixture available from Degussa Care & Surface Specialties, Hopewell, VA.
*17 Behenyltrimethylammonium chloride in carrier available from Sanyo Performance Chemicals, JP.
*18 Hexamidine diisethionate, availabile from Laboratoires Serobiologiques.
*19 DMDM Hydrantoin and Iodopropynyl Butylcarbamate blend available from Lonza, Inc.
*20 Available from Ajinomoto U.S.A., Inc., Paramus NJ.
*21 $TiO_2$ with water, glycerine, polyacrylate, and methylparaben available from Kobo Products.
*22 Polyacrylamide, C13-14 Isoparaffin, and Laureth-7 blend from Seppic.
*23 As described in aforementioned "Improved Efficacy Test"

For example 1, combine the ingredients of Phase A in a suitable container. In a separate suitable container, combine the ingredients of Phase B. Heat each phase to 75-80° C. while mixing each phase using a suitable mixer (e.g., Anchor blade, propeller blade) until each reaches temperature and is homogenous. Slowly add Phase B to Phase A while continuing to mix Phase A. Continue mixing until batch is uniform. Homogenize product with Ultra-Turrax homogenizer (IKA, Inc) or equivalent and pour product into suitable containers at 75-80° C. Store the containers at room temperature without disturbing for at least 12 hours.

For examples 2-4, 7-10, and 12, in a suitable container, combine the ingredients of Phase A and mix with a suitable mixer (with heat if needed) until homogenous. In a separate container, combine the ingredients of Phase B and mix with a suitable mixer (with heat if needed) until homogenous. Slowly add Phase B to Phase A while continuing to mix Phase A. Continue mixing (with heat if needed) until batch is uniform. Homogenize product with Ultra-Turrax homogenizer (IKA, Inc) or equivalent and pour product into suitable containers.

For examples 5-6 and 11, in a suitable vessel, the ingredients are combined and mixed (with heat if needed) until uniform; the composition may be warmed to dissolve all ingredients. Once the composition is uniform, the product is poured into suitable containers.

Examples 13 and 14 may be used as a body cleansing composition.

| (values are weight %) | 13 | 14 |
|---|---|---|
| Cocoamidopropyl betaine | 5.15 | 5.15 |
| Sodium Laureth sulfate | 5.8 | 5.8 |
| Sodium Lauroyl sarcosinate | 0.5 | 0.5 |
| Polyquaternium 10 | 0.1 | 0.1 |
| C12-14 fatty alcohol | 0.45 | 0.45 |

-continued

| (values are weight %) | 13 | 14 |
|---|---|---|
| Zinc Stearate | 1.5 | 1.5 |
| Glycol Distearate | 0.25 | 0.25 |
| Sodium lauryl sulfate | 0.53 | 0.53 |
| Cocoamidopropyl betaine | 0.17 | 0.17 |
| Lauramide Diethanolamide | 0.48 | 0.48 |
| Sodium sulfate | 0.05 | 0.05 |
| Citric Acid | 0.05 | 0.05 |
| DMDM hydantoin (1,3-Dimethylol-5,5-dimethylhydantoin Glydant) | 0.2 | 0.2 |
| Tetra Sodium EDTA | 0.1 | 0.1 |
| Fragrance | 0.5 | 0.5 |
| Polysaccharide (Xanthan Gum-glyoxal modified Optixan-T) | 0.2 | 0.2 |
| Abrasive Particle A and/or B | 2 | 1 |
| Water | Balance | Balance |

Examples 15-18 may be used a facial cleansing composition.

| (values are weight %) | 15 | 16 | 17 | 18 |
|---|---|---|---|---|
| Acrylates Copolymer*1 | 1.50 | 2.0 | 1.25 | — |
| Acrylates/C10-30 alkyl acrylate crosspolymer*2 | — | — | — | 1.0 |
| Sodium Lauryl Sulfate | 2.0 | — | — | — |
| Sodium Laureth Sulfate | 8.0 | — | — | — |
| Ammonium Lauryl Sulfate | — | 6.0 | — | — |
| Sodium Trideceth Sulfate | — | — | 3.0 | 2.5 |
| Sodium Myristoyl Sarcosinate | — | 2.0 | 3.0 | 2.5 |
| Sodium Lauroamphoacetate*3 | — | — | 6.0 | 5.0 |
| Sodium Hydroxide* | pH > 6 | — | — | — |
| Triethanolamine* | — | pH > 6 | — | pH 5.2 |
| Cocamidopropyl Betaine | 4.0 | 7.0 | — | — |
| Glycerin | 4.0 | 5.0 | 2.0 | 2.0 |
| Sorbitol | — | — | 2.0 | 2.0 |
| Salicylic Acid | — | — | 2.0 | 2.0 |
| Fragrance | 0.1 | 0.1 | 0.1 | 0.1 |

| (values are weight %) | 15 | 16 | 17 | 18 |
|---|---|---|---|---|
| Preservative | 0.3 | 0.3 | 0.15 | 0.15 |
| Abrasive Particle A and/or B | 1.0 | 1.0 | 2.0 | 2.0 |
| PEG 120 Methyl Glucose Trioleate*4 | 0.5 | — | 0.25 | 0.25 |
| PEG 150 Pentaerythrityl Tetrastearate*5 | — | 0.40 | — | — |
| Citric Acid** | pH 5.5 | pH 5.5 | pH 5.5 | pH 5.5 |
| Water | QS to 100% | QS to 100% | QS to 100% | QS to 100% |

*per the supplier use directions, the base is used to activate the acrylates copolymer
**acid can be added to adjust the formula to a lower pH
*1Carbopol Aqua SF-1 ® from Noveon™, Inc.
*2Carbopol Ultrez 21 ® from Noveon™, Inc.
*3Miranol ® Ultra L32 from Rhodia
*4Glucamate LT ® from Chemron
*5Crothix ® from Croda For Examples 15-18, add Carbopol® to de-ionized free water of the formulation. Add all surfactants except cationics and betaines. If the pH is less than 6 then add a neutralizing agent (typically a base i.e., Triethanolamine, sodium hydroxide) to adjust to a pH greater than 6. If necessary, apply gentle heat to reduce viscosity and help minimize air entrapment. Add betaine and/or cationic surfactants. Add conditioning agents, additional rheology modifiers, pearlizing agents, encapsulated materials, exfoliants, preservatives, dyes, fragrances, abrasive particles and other desirable ingredients. Lastly, if desired reduce the pH with an acid (i.e. citric acid) and increase viscosity by adding sodium chloride.

Methods of Using the Personal Care Compositions

The personal care compositions of the present invention may be useful for improving or regulating a number of keratinous tissue conditions. As used in relation to methods of using the personal care compositions, "regulating" means maintaining skin appearance and/or feel of the keratinous tissue with little to no degradation in appearance and/or feel, and "improving" means affecting a positive change in keratinous tissue appearance and/or feel. The keratinous tissue appearance and/or feel benefit may be an acute or chronic benefit.

Keratinous tissue conditions that may be regulated or improved include, but are not limited to thickening keratinous tissue (e.g., building the epidermis and/or dermis and/or subcutaneous layers of the skin or lips and where applicable the keratinous layers of the nail and hair shaft including eye lashes), atrophy, softening and/or smoothing, itch, appearance of dark under-eye circles and/or puffy eyes, sallowness, sagging (e.g., glycation), tanning, desquamating, exfoliating, and/or increasing turnover in mammalian skin, pores size, oily/shiny appearance, hyperpigmentation such as post-inflammatory hyperpigmentation, spider vessels and/or red blotchiness on mammalian skin, fine lines and wrinkles, dryness (e.g., roughness, scaling, flaking), cellulite, and acne.

Other keratinous conditions that may be regulated or improved include signs of skin aging including, but not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

The personal care compositions of the present invention may be useful for improving or regulating insult-affected keratinous tissue. "Insult-affected keratinous tissue," means keratinous tissue which exhibits discomfort, irritation, an unpleasant or irregular appearance, and the like, for example after exposure to a physical and/or chemical irritant. Non-limiting examples of insult-affected keratinous tissue include burn (e.g., sunburns, windburn, chemical or thermal burns); rashes (e.g., diaper rash, shaving rash and allergen-induced rashes); discoloration (e.g., bleaching, staining, hyperpigmentation); nicks and cuts (e.g., shaving insults); and dry, chapped or rough skin (e.g., due to exposure to example wind, cold and/or low humidity). Non-limiting examples of insults include radiation, wind, low humidity, allergens, pollutants, chemical and natural irritants, bodily fluids, bodily waste, excessive moisture, bacteria, fungi, etc.

Regulating and improving keratinous tissue condition involves topically applying to the keratinous tissue a safe and effective amount of a composition of the present invention. The amount of the composition that is applied, the frequency of application and the period of use will vary widely depending upon the actives and other components of a given composition and the level of regulation or improvement desired.

In certain embodiments, the composition is chronically applied to the keratinous tissue and, more specifically, the skin. By "chronic topical application" is meant routine or periodic application of the composition over a time period during the subject's lifetime. Suitable time periods include at least about one week, at least about one month, at least about three months, at least about six months, and at least about one year. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions, which are typically applied per application, are, in mg of composition per $cm^2$ of keratinous tissue and, more specifically, the skin. A suitable application quantity is from about 0.1 $mg/cm^2$ to about 20 $mg/cm^2$ or from about 0.5 $mg/cm^2$ to about 10 $mg/cm^2$.

Suitable keratinous tissues to which the compositions may be employed include any part of the external portion of the face, hair, and/or nails. For example, the personal care composition may be applied to the face, lips, under-eye area, eyelids, scalp, neck, torso, arms, hands, legs, fingernails, toenails, scalp hair, eyelashes, eyebrows, and the like. In one embodiment the personal care composition is applied to a "facial skin surface," which refers to one or more of the forehead, periorbital, cheek, perioral, chin, and nose skin surfaces.

When in the form of a leave-on, the personal care compositions may be left on the keratinous tissue for a period of at least about 15 minutes, at least about 30 minutes, at least about 1 hour, or for several hours (e.g., over 12 hours).

The application of the present compositions may be done using, e.g., the palms of the hands and/or fingers, an implement, e.g., a cotton ball, swab, pad etc.

The composition can be dispensed from a bottle, jar, tube, sachet, pouch, container, bottle, vial, ampoule, compact, etc. or can be integrally contained within a delivery form such as a wipe.

The application of the present compositions may be done using the palms of the hands and/or fingers. The application may also be done with the aid of a device or implement such as a cotton ball, swab, pad, brush, eye dropper, puff, sponge, wand, wipe, foam, nonwoven substrate, mask, roll-on applicator, stick applicator, applicator pen, spray applicator, atomizer, razor, etc. The active may be contained in a rupturable pouch between two substrates.

Test Methods

1. Turbidity (NTU)—The turbidity (measured in NTU: Nephelometric Turbidity Units) is measured using a Hach 2100P turbidity meter calibrated according to the procedure provided by the manufacture. The sample vials are filled with 15 ml of representative sample and capped and cleaned according to the operating instructions. If necessary, the samples are degassed to remove any bubbles either by applying a vacuum or using an ultrasonic bath (see operating manual for procedure). The turbidity is measured using the automatic range selection.

2. Viscosity—Viscosities are measured on a Brookfield viscometer using a T-C bar spindle with a heliopath setting at 5 rpm at 25° C.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition in the form of an emulsion for cleansing keratinous tissue, comprising:
    a) an aqueous phase;
    b) an oil phase;
    c) about 0.3% to about 10%, by weight of the composition, of abrasive particles having three or more parameters selected from the group consisting of:
        i) a mean Equivalent Circle diameter of between 10 μm to 1000 μm;
        ii) a mean Circularity between 0.10 to 0.50;
        iii) a mean Solidity between 0.40 to 0.90;
        iv) a mean Roughness between 0.05 to 0.30;
        v) a packing density between 10 kg/m$^3$ to 250 kg/m$^3$; and
        vi) a hardness of between 5 kg/mm$^2$ to 50 kg/mm$^2$;
    d) about 1% to 10%, by weight of the composition, of a dermatologically acceptable detersive surfactant; and
    e) a dermatologically acceptable carrier.

2. The personal care composition of claim 1 wherein the abrasive particles comprise:
    a) a mean Equivalent Circle diameter between 75 μm to 350 μm;
    b) a mean Circularity between 0.35 to 0.45;
    c) a mean Solidity between 0.70 to 0.90;
    d) a mean Roughness between 0.05 to 0.15;
    e) a packing density between 60 kg/m$^3$ to 120 kg/m$^3$; and
    f) a hardness between 15 kg/mm$^2$ to 25 kg/mm$^2$.

3. The personal care composition of claim 1 wherein the composition comprises from about 1% to about 95%, by weight of the composition, water and about 1% to about 95%, by weight of the composition, oil.

4. The personal care composition of claim 3 wherein the oil is selected from the group consisting of linear silicones, cyclic silicones, paraffinic hydrocarbons, fatty esters, hydrocarbon oils, cationic silicone fluids, and combinations thereof.

5. The personal care composition of claim 1 further comprising a structuring agent selected from the group consisting of polysaccharides, gums, carboxylic acid polymers, sulfonated polymers, acrylamide polymers, polyalkylglycols, polyglycerins, silicone elastomers, silicone gums, silicone waxes, polyamides, polysilicone-polyamide copolymers, natural and synthetic waxes, natural and synthetic montmorillonite minerals, silicas, silicates, and combinations thereof.

6. The personal care composition of claim 1 further comprising an active or agent selected from the group consisting of sugar amines, vitamins, oil control agents, phytosterols, hexamidine compounds, tightening agents, anti-wrinkle actives, anti-atrophy actives, flavonoids, N-acyl amino acid compounds, retinoids, peptides, UV actives, photo stabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, and combinations thereof.

7. The personal care composition of claim 6 wherein the vitamins are selected from the group consisting of vitamin B3 compound, ascorbic acid, tocopherol acetate, panthenol, dexpanthenol, magnesium ascorbyl phosphate, sodium ascorbyl phosphate, retinyl propionate, and combinations thereof.

8. The personal care composition of claim 6 wherein the active or agent is selected from glucosamine, salts of dehydroacetic acid, salicylic acid, hexamidine diisethionate, salts of dialkanoyl hydroxyproline, N-acyl phenylalanine, dipeptides, pentapeptides, titanium dioxide, iron oxide, zinc oxide, butylated hydroxytoluene, dihydroxyacetone, and combinations thereof.

9. The personal care composition of claim 1 wherein the composition is paraben free.

10. The personal care composition of claim 1 wherein the abrasive particles comprise a reduced foamed polymer.

11. The personal care composition of claim 10 wherein the polymer is selected from the group consisting of polystyrene, polyurethane, and a melamine resin.

12. The personal care composition of claim 1 wherein the abrasive particles are obtained by reducing foam obtained through a polymerized high internal phase emulsion.

* * * * *